US008137318B2

(12) United States Patent
Schweitzer et al.

(10) Patent No.: US 8,137,318 B2
(45) Date of Patent: Mar. 20, 2012

(54) SURGICAL PROTECTION DEVICE FOR A SURGICAL SEALING ELEMENT AND SURGICAL SEALING SYSTEM

(75) Inventors: Tom Schweitzer, Tuttlingen (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 103 days.

(21) Appl. No.: 12/459,944

(22) Filed: Jul. 8, 2009

(65) Prior Publication Data
US 2010/0016799 A1 Jan. 21, 2010

(30) Foreign Application Priority Data

Jul. 9, 2008 (DE) .......................... 10 2008 033 374

(51) Int. Cl.
*A61M 5/178* (2006.01)
(52) U.S. Cl. .......... 604/167.01; 604/167.02; 604/167.06
(58) Field of Classification Search ............. 604/164.01, 604/164.02, 167.01, 167.02, 167.03, 167.04, 604/167.06, 236–237
See application file for complete search history.

(56) References Cited

U.S. PATENT DOCUMENTS

| 3,712,298 A | 1/1973 | Snowdon et al. |
| 3,845,766 A | 11/1974 | Zoller |
| 4,265,694 A | 5/1981 | Boretos et al. |
| 4,924,923 A | 5/1990 | Boehmer et al. |
| 4,929,235 A | 5/1990 | Merry et al. |
| 5,104,382 A | 4/1992 | Brinkerhoff et al. |
| 5,114,407 A | 5/1992 | Burbank |
| 5,127,626 A | 7/1992 | Hilal et al. |
| 5,141,498 A | 8/1992 | Christian |
| 5,174,613 A | 12/1992 | Joug |
| 5,180,373 A | 1/1993 | Green et al. |
| 5,197,955 A | 3/1993 | Stephens et al. |
| 5,203,773 A | 4/1993 | Green |
| 5,209,737 A | 5/1993 | Ritchart et al. |
| 5,256,147 A | 10/1993 | Vidal et al. |

(Continued)

FOREIGN PATENT DOCUMENTS

CA    2 504 540    4/2005

(Continued)

OTHER PUBLICATIONS

Aesculap brochure, "MIT-System, Multi Interchangeable Trocar-System", 3 pages (undated).

*Primary Examiner* — Nicholas Lucchesi
*Assistant Examiner* — Quynh-Nhu H Vu
(74) *Attorney, Agent, or Firm* — Lipsitz & McAllister, LLC

(57) ABSTRACT

In order to improve a surgical protection device for a surgical sealing element of a surgical sealing system comprising a trocar, the sealing element having an insertion opening which can be widened, the protection device comprising a base member which can be arranged on the trocar or on a part thereof, is closed in a ring shape and has an opening and several protection elements which are arranged in circumferential direction and point parallel or towards a longitudinal axis of the protection device, the protection elements having free ends pointing essentially in a distal direction, such that protection of the sealing element can be as complete as possible irrespective of the degree of expansion thereof, it is suggested that at least some of the protection elements have retaining elements on an outer side at their free ends or in the area of their free ends for engagement with the sealing element.

Furthermore, an improved surgical sealing system is suggested.

50 Claims, 16 Drawing Sheets

U.S. PATENT DOCUMENTS

| | | | |
|---|---|---|---|
| 5,261,891 A | 11/1993 | Brinkerhoff et al. | |
| 5,267,965 A | 12/1993 | Deniega | |
| 5,269,763 A | 12/1993 | Boehmer et al. | |
| 5,295,993 A | 3/1994 | Green | |
| 5,304,143 A | 4/1994 | Green et al. | |
| 5,308,336 A | 5/1994 | Hart et al. | |
| 5,314,417 A | 5/1994 | Stephens et al. | |
| 5,318,585 A | 6/1994 | Guy et al. | |
| 5,330,437 A | 7/1994 | Durman | |
| 5,338,305 A | 8/1994 | Plyley et al. | |
| 5,342,315 A * | 8/1994 | Rowe et al. | 604/167.06 |
| 5,342,382 A | 8/1994 | Brinkerhoff et al. | |
| 5,356,421 A | 10/1994 | Castro | |
| 5,385,553 A | 1/1995 | Hart et al. | |
| 5,387,197 A | 2/1995 | Smith et al. | |
| 5,399,167 A | 3/1995 | Deniega | |
| 5,405,328 A | 4/1995 | Vidal et al. | |
| 5,441,041 A | 8/1995 | Sauer et al. | |
| 5,462,532 A | 10/1995 | Gresl | |
| 5,467,762 A | 11/1995 | Sauer et al. | |
| 5,474,539 A | 12/1995 | Costa et al. | |
| 5,476,475 A | 12/1995 | Gadberry | |
| 5,486,190 A | 1/1996 | Green | |
| 5,522,833 A | 6/1996 | Stephens et al. | |
| 5,534,009 A | 7/1996 | Lander | |
| 5,569,160 A | 10/1996 | Sauer et al. | |
| 5,569,292 A | 10/1996 | Scwemberger et al. | |
| 5,584,850 A | 12/1996 | Hart et al. | |
| 5,609,604 A | 3/1997 | Schwemberger et al. | |
| 5,618,297 A | 4/1997 | Hart et al. | |
| 5,626,598 A | 5/1997 | Roth | |
| 5,658,236 A | 8/1997 | Sauer et al. | |
| 5,662,615 A | 9/1997 | Blake, III | |
| 5,669,885 A | 9/1997 | Smith | |
| 5,685,854 A | 11/1997 | Green et al. | |
| 5,690,663 A | 11/1997 | Stephens | |
| 5,690,664 A | 11/1997 | Sauer et al. | |
| 5,709,671 A | 1/1998 | Stephens et al. | |
| 5,752,938 A | 5/1998 | Flatland et al. | |
| 5,776,112 A | 7/1998 | Stephens et al. | |
| 5,782,812 A | 7/1998 | Hart et al. | |
| 5,792,113 A | 8/1998 | Kramer et al. | |
| 5,803,919 A | 9/1998 | Hart et al. | |
| 5,807,338 A | 9/1998 | Smith et al. | |
| 5,817,061 A | 10/1998 | Goodwin et al. | |
| 5,851,216 A | 12/1998 | Allen | |
| 5,860,996 A | 1/1999 | Urban et al. | |
| 5,865,807 A | 2/1999 | Blake, III | |
| 5,879,332 A | 3/1999 | Schwemberger et al. | |
| 5,895,377 A * | 4/1999 | Smith et al. | 604/256 |
| 5,904,699 A | 5/1999 | Schwemberger et al. | |
| 5,906,595 A | 5/1999 | Powell et al. | |
| 5,916,232 A | 6/1999 | Hart | |
| 5,947,930 A | 9/1999 | Schwemberger et al. | |
| 5,980,493 A | 11/1999 | Smith et al. | |
| 5,989,224 A | 11/1999 | Exline et al. | |
| 5,997,510 A | 12/1999 | Schwemberger | |
| 6,004,326 A | 12/1999 | Castro et al. | |
| 6,197,041 B1 | 3/2001 | Shichman et al. | |
| 6,319,266 B1 | 11/2001 | Stellon et al. | |
| 6,497,716 B1 | 12/2002 | Green et al. | |
| 6,551,282 B1 | 4/2003 | Exline et al. | |
| 6,685,630 B2 | 2/2004 | Sauer et al. | |
| 6,702,787 B2 | 3/2004 | Racenet et al. | |
| 7,169,130 B2 | 1/2007 | Exline et al. | |
| 7,390,317 B2 | 6/2008 | Taylor et al. | |
| 7,731,694 B2 | 6/2010 | Becker et al. | |
| 2001/0042927 A1 | 11/2001 | Rock | |
| 2002/0026207 A1 | 2/2002 | Stellon et al. | |
| 2002/0156432 A1 | 10/2002 | Racenet et al. | |
| 2003/0195541 A1 | 10/2003 | Exline et al. | |
| 2004/0059297 A1 | 3/2004 | Racenet et al. | |
| 2004/0106942 A1 | 6/2004 | Taylor et al. | |
| 2004/0111060 A1 | 6/2004 | Racenet et al. | |
| 2004/0162531 A1 | 8/2004 | Wenchell | |
| 2004/0215209 A1 | 10/2004 | Almond et al. | |
| 2004/0230161 A1 | 11/2004 | Zeiner | |
| 2004/0260244 A1 | 12/2004 | Piechowicz et al. | |
| 2005/0033342 A1 | 2/2005 | Hart et al. | |
| 2005/0065543 A1 | 3/2005 | Kahle et al. | |
| 2005/0070943 A1 | 3/2005 | Hueil et al. | |
| 2005/0077688 A1 | 4/2005 | Voegele et al. | |
| 2005/0077689 A1 | 4/2005 | Hueil | |
| 2005/0107816 A1 | 5/2005 | Pingleton et al. | |
| 2005/0131349 A1 | 6/2005 | Albrecht et al. | |
| 2005/0251191 A1 | 11/2005 | Taylor et al. | |
| 2005/0288622 A1 | 12/2005 | Albrecht et al. | |
| 2005/0288634 A1 | 12/2005 | O'Heeron et al. | |
| 2006/0211992 A1 | 9/2006 | Prosek | |
| 2006/0217665 A1 | 9/2006 | Prosek | |
| 2006/0229654 A1 | 10/2006 | Voegele et al. | |
| 2006/0229655 A1 | 10/2006 | Voegele et al. | |
| 2007/0088277 A1 | 4/2007 | McGinley et al. | |
| 2007/0185453 A1 | 8/2007 | Michael et al. | |
| 2007/0255218 A1 | 11/2007 | Franer | |
| 2008/0249475 A1 | 10/2008 | Albrecht et al. | |
| 2009/0082735 A1 | 3/2009 | Schweitzer et al. | |

FOREIGN PATENT DOCUMENTS

| | | |
|---|---|---|
| DE | 43 03 026 | 8/1994 |
| DE | 692 22 688 | 3/1998 |
| DE | 696 02 111 | 4/1999 |
| DE | 693 23 750 | 10/1999 |
| DE | 102 14 552 | 10/2003 |
| DE | 20 2006 005 442 | 6/2006 |
| DE | 698 38 231 | 5/2008 |
| EP | 0 426 407 | 5/1991 |
| EP | 0 474 124 | 3/1992 |
| EP | 0 495 633 | 7/1992 |
| EP | 0 495 634 | 7/1992 |
| EP | 0 552 851 | 7/1993 |
| EP | 0 350 291 | 9/1994 |
| EP | 0 312 219 | 12/1994 |
| EP | 0 479 130 | 12/1994 |
| EP | 0 520 296 | 4/1995 |
| EP | 0 494 520 | 9/1995 |
| EP | 0 696 459 | 2/1996 |
| EP | 0 511 676 | 7/1996 |
| EP | 0 499 457 | 5/1997 |
| EP | 0 567 142 | 7/1997 |
| EP | 0 517 248 | 10/1997 |
| EP | 0 617 924 | 10/1997 |
| EP | 0 642 764 | 12/1997 |
| EP | 0 630 213 | 1/1998 |
| EP | 0 594 687 | 4/1998 |
| EP | 0 600 921 | 5/1998 |
| EP | 0 649 634 | 9/1998 |
| EP | 0 697 838 | 9/1998 |
| EP | 0 630 619 | 10/1998 |
| EP | 0 648 096 | 11/1998 |
| EP | 0 768 063 | 2/1999 |
| EP | 0 652 730 | 3/1999 |
| EP | 0 724 864 | 4/1999 |
| EP | 0 591 851 | 6/1999 |
| EP | 0 684 016 | 12/1999 |
| EP | 0 768 064 | 12/1999 |
| EP | 0 604 197 | 2/2000 |
| EP | 0 614 384 | 2/2000 |
| EP | 0 701 799 | 3/2000 |
| EP | 0 716 862 | 8/2001 |
| EP | 0 994 740 | 7/2003 |
| EP | 0 785 756 | 9/2003 |
| EP | 1 058 566 | 10/2003 |
| EP | 0 769 278 | 1/2004 |
| EP | 0 807 414 | 1/2004 |
| EP | 1 402 827 | 3/2004 |
| EP | 1 459 688 | 9/2004 |
| EP | 0 867 150 | 11/2004 |
| EP | 1 350 476 | 4/2005 |
| EP | 1 520 541 | 4/2005 |
| EP | 0 873 721 | 12/2005 |
| EP | 1 625 863 | 2/2006 |
| EP | 1 671 596 | 6/2006 |
| EP | 1 707 136 | 10/2006 |
| EP | 1 707 137 | 10/2006 |
| EP | 1716813 | 11/2006 |
| EP | 1 520 544 | 6/2007 |

| | | |
|---|---|---|
| EP | 1 582 158 | 12/2007 |
| EP | 1 889 580 | 2/2008 |
| GB | 1 466 242 | 3/1977 |
| WO | 93/01850 | 2/1993 |
| WO | 93/04632 | 3/1993 |
| WO | 93/04715 | 3/1993 |
| WO | 95/07663 | 3/1995 |
| WO | 95/15189 | 6/1995 |
| WO | 96/11640 | 4/1996 |
| WO | 98/50093 | 11/1998 |
| WO | 99/12481 | 3/1999 |
| WO | 99/52577 | 10/1999 |
| WO | 00/54679 | 9/2000 |
| WO | 01/89397 | 11/2001 |
| WO | 02/41795 | 5/2002 |
| WO | 03/026512 | 4/2003 |
| WO | 03/043683 | 5/2003 |
| WO | 03/096879 | 11/2003 |
| WO | 2004/096295 | 11/2004 |
| WO | 1 520 539 | 4/2005 |
| WO | 2005/032348 | 4/2005 |
| WO | 2005/053783 | 6/2005 |
| WO | 2005/060844 | 7/2005 |
| WO | 2005/112799 | 12/2005 |
| WO | 2006/004652 | 1/2006 |
| WO | 2006/119197 | 11/2006 |
| WO | 2007/098495 | 8/2007 |
| WO | 2007/110371 | 10/2007 |
| WO | 2007/121425 | 10/2007 |

* cited by examiner

US 8,137,318 B2

SURGICAL PROTECTION DEVICE FOR A SURGICAL SEALING ELEMENT AND SURGICAL SEALING SYSTEM

CROSS-REFERENCE TO RELATED APPLICATIONS

The present disclosure relates to the subject matter disclosed in German application number 10 2008 033 374.3 of Jul. 9, 2008, which is incorporated herein by reference in its entirety and for all purposes.

FIELD OF THE INVENTION

The present invention relates to a surgical protection device for a surgical sealing element of a surgical sealing system generally, and more specifically to a surgical protection device for a surgical sealing element of a surgical sealing system which comprises a trocar, the sealing element having an insertion opening which can be widened, the protection device comprising a base member which can be arranged on the trocar or on a part thereof, is of a ring shape or essentially of a ring shape and defines an opening and has several protection elements which are arranged in circumferential direction and point parallel or towards a longitudinal axis of the protection device, the protection elements having free ends pointing essentially in a distal direction.

Furthermore, the present invention relates to a surgical sealing system generally, and more specifically to a surgical sealing system, comprising a trocar with a trocar sleeve, a surgical sealing element, which is held on the trocar sleeve and has an insertion opening which can be widened, for sealing the insertion opening during insertion of a surgical instrument and a surgical protection device for the sealing element, the protection device comprising a base member which can be arranged on the trocar or on the sealing element, is in a ring shape or essentially in a ring shape and defines an opening and has several protection elements which are arranged in circumferential direction and point parallel or towards a longitudinal axis of the protection device, the protection elements having free ends pointing essentially in a distal direction.

BACKGROUND OF THE INVENTION

A protection device as well as a sealing system of the type described at the outset are known, for example, from EP 0 696 459 B1. The protection device serves the purpose of protecting the sealing element, which is often produced from an elastic material, during the insertion of instruments with pointed ends into the trocar. Sharp ends of instruments, for example, tips and edges on tool elements of the instruments can lead to the instrument tip becoming caught up in the sealing element and, therefore, the insertion of the instrument will be made more difficult or even impossible. In the most unfavorable case, the sealing element can even be destroyed. In addition, the protection elements have the advantage that they aid an elastic expansion of the insertion opening in the case of instruments with large diameters. The known, lamellar protection elements normally rest on the sealing element and so a disadvantageous relative movement between the protection element and the sealing element can result, in particular, during the insertion of an instrument through the insertion opening of the sealing element.

One disadvantage of the known protection devices is the fact that the protection elements do not always reach exactly as far as the sealing area. It is, therefore, possible for unprotected areas of the sealing element to remain which can be damaged by sharp ends of instruments.

It is, therefore, an object of the invention to improve a surgical protection device as well as a surgical sealing system of the type described at the outset such that protection of the sealing element can be as complete as possible irrespective of the degree of expansion thereof.

SUMMARY OF THE INVENTION

In a first aspect of the invention, a surgical protection device is provided for a surgical sealing element of a surgical sealing system comprising a trocar. The sealing element has an insertion opening adapted to be widened. The protection device comprises a base member adapted to be arranged on the trocar or on a part thereof, being in a ring shape or essentially in a ring shape and defining an opening and comprising several protection elements arranged in circumferential direction and pointing parallel or towards a longitudinal axis of the protection device. The protection elements have free ends pointing essentially in a distal direction. At least some of the protection elements have at least one retaining element on an outer side at their free ends or in the area of their free ends for engagement with the sealing element.

In a second aspect of the invention, a surgical sealing system is provided. The surgical sealing system comprises a trocar with a trocar sleeve, a surgical sealing element having an insertion opening adapted to be widened and being held on the trocar sleeve for sealing the insertion opening during insertion of a surgical instrument and a surgical protection device for the sealing element. The protection device comprises a base member adapted to be arranged on the trocar or on the sealing element, being in a ring shape or essentially in a ring shape and defining an opening and having several protection elements arranged in circumferential direction and pointing parallel or towards a longitudinal axis of the protection device. The protection elements have free ends pointing essentially in a distal direction. At least some of the protection elements have at least one retaining element on an outer side at their free ends or in the area of their free ends for engagement with the sealing element.

BRIEF DESCRIPTION OF THE DRAWINGS

The foregoing summary and the following description may be better understood in conjunction with the drawing figures, of which.

DETAILED DESCRIPTION OF PREFERRED EMBODIMENTS OF THE INVENTION

Figure 1:
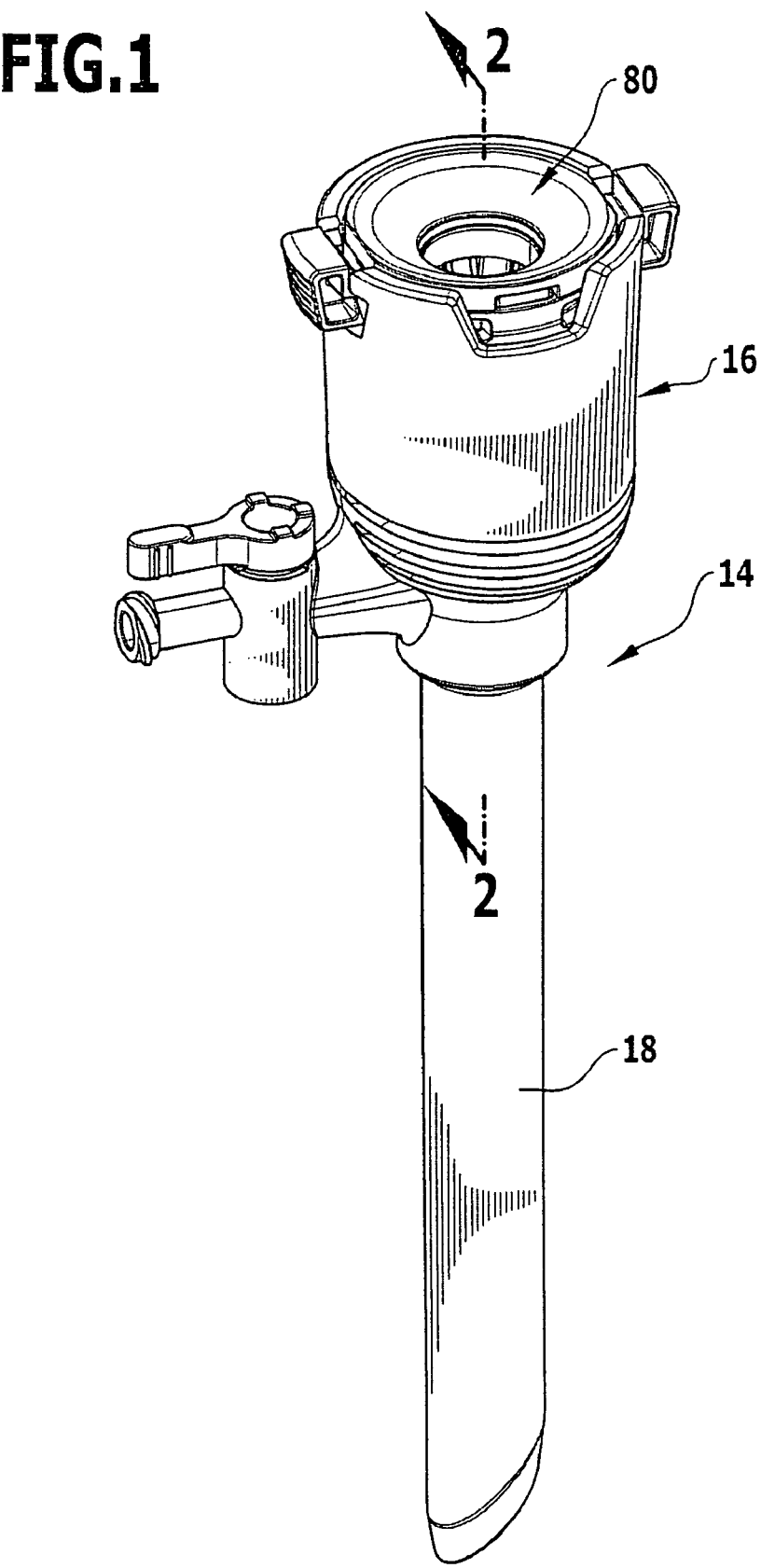
FIG. 1: shows a perspective overall view of a surgical sealing system.
Figure 2:
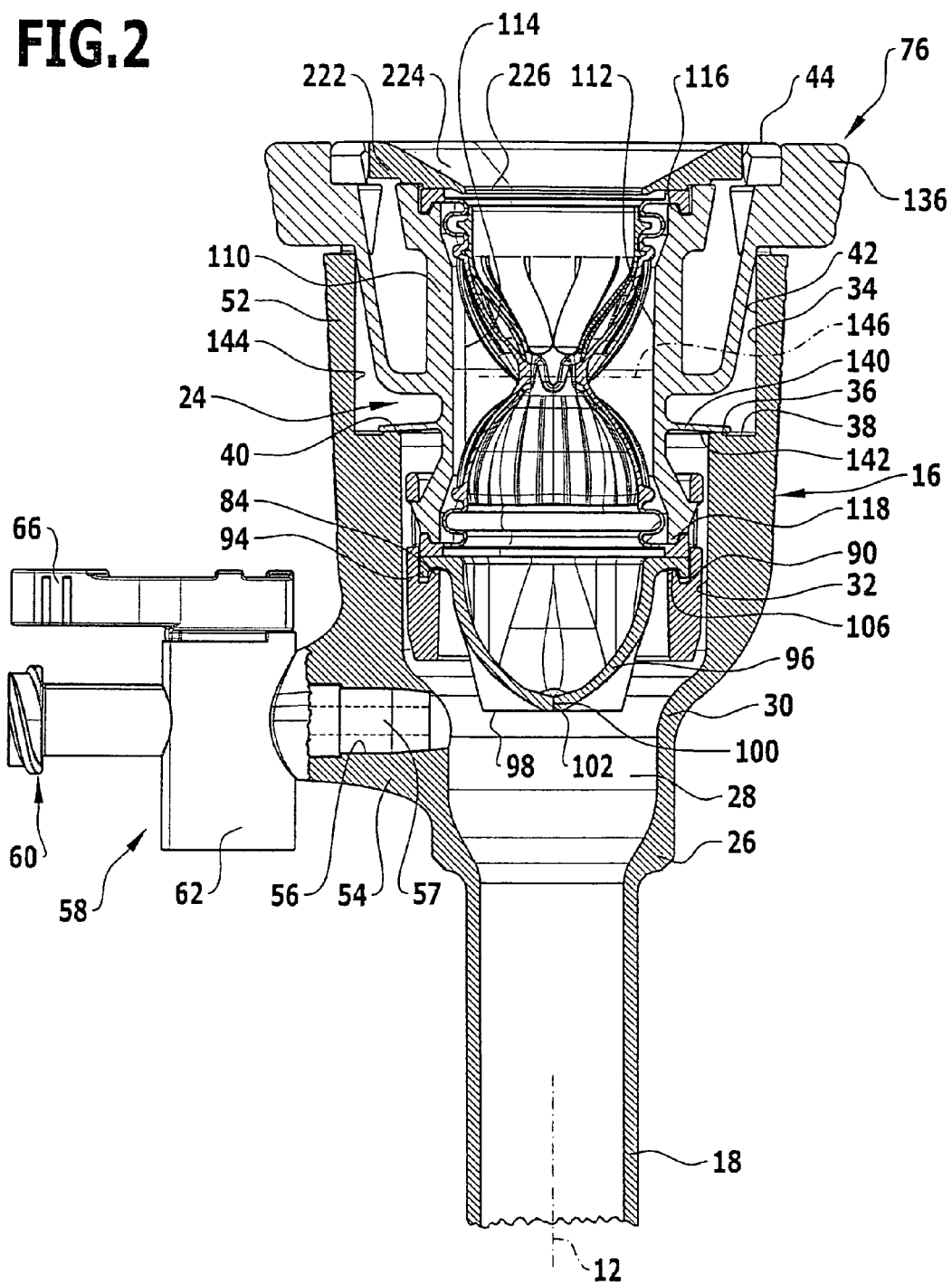
FIG. 2: shows a sectional view along line 2-2 in FIG. 1.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical protection device for a surgical sealing element of a surgical sealing system comprising a trocar, the sealing element having an insertion opening adapted to be widened, the protection device comprising a base member adapted to be arranged on the trocar or on a part thereof, being in a ring shape or essentially in a ring shape and defining an opening and comprising several protection elements arranged in circumferential direction and pointing parallel or towards a longitudinal axis of the protection device, the protection elements having free ends pointing essentially in a distal direction, wherein at least some of the protection elements have at least one retaining element on an outer side at their free ends or in the area of their free ends for engagement with the sealing element Moreover, the present invention relates to a surgical sealing system comprising a trocar with a trocar sleeve, a surgical sealing element having an insertion opening adapted to be widened and being held on the trocar sleeve for sealing the insertion opening during insertion of a surgical instrument and a surgical protection device for the sealing element, the protection device comprising a base member adapted to be arranged on the trocar or on the sealing element, being in a ring shape or essentially in a ring shape and defining an opening and having several protection elements arranged in circumferential direction and pointing parallel or towards a longitudinal axis of the protection device, said protection elements having free ends pointing essentially in a distal direction, wherein at least some of the protection elements have at least one retaining element on an outer side at their free ends or in the area of their free ends for engagement with the sealing element The proposed further development of the known protection device as well as the known sealing system has the advantage, in particular, that it is specifically possible for the protection device to become caught up in the sealing element which is precisely what should be avoided during the insertion of the instruments. During the insertion of the instruments, the fact that the retaining elements are brought into engagement with the sealing element has the advantage that it can be ensured in this way that protection of the sealing element can be ensured up to the area of the sealing element which abuts on the inserted instrument shaft, i.e., in particular, a defined sealing line or sealing lip. As a result of the retaining elements being brought into engagement with the sealing element, a widening of the insertion opening of the protection device automatically leads to an elastic expansion of the sealing element, as well. Any relative movement of the protection device and the sealing element is, however, essentially prevented. This has the advantage that a covering of the sealing element from the time the retaining elements are brought into engagement with the sealing element can be ensured in an axial direction of the protection device irrespective of an insertion position of the instrument inserted. Engagement can be brought about, in particular, when the retaining element has a minimum diameter so that when it impinges on, for example, a sealing element produced from an elastomer it causes a bulge in its wall and thus defines, as it were, a corresponding recess, in which the retaining element engages. As a result of the bulging, the object causing a bulge in the sealing element will, however, be prevented from sliding along on the sealing element. A single retaining element is preferably provided on the respective protection elements. In principle, it would also be conceivable to provide several retaining elements, i.e., two, three or more on a respective protection element in order to prevent any relative movement between the retaining elements and the sealing element when the sealing element is unfolded for the purpose of widening the insertion opening as a result of the two parts being brought into engagement.

It is favorable when the at least one retaining element is designed in the form of a retaining projection protruding from the protection element. Retaining elements of this type are particularly easy to produce and can be dimensioned accordingly in order to ensure that the retaining projections become specifically caught in or are otherwise brought into engagement with the sealing element.

Depending on the orientation of the protection elements in a basic position or also a widened position, it is advantageous when at least some of the retaining projections protrude from the protection elements at right angles or essentially at right angles. In addition, such a configuration of the retaining projections is particularly easy to produce.

Catching or engagement of the retaining projections in or with the sealing element can be improved, particularly when the protection elements protrude parallel to a longitudinal axis defined by the sealing element on the base member, when at least some of the retaining projections protrude away from the protection elements in the area of their free ends at an angle in relation to an extension of the projection elements. In particular, retaining projections of this type point away from the base member and outwards in a direction towards the sealing element. It can thus be ensured in a simple and reliable manner that the retaining projections become caught in the sealing element.

A diameter of the retaining elements is preferably at the most 1 mm. Depending on the size as well as on a wall thickness of the sealing element, it can, however, also be advantageous when a diameter of the retaining elements is at the most 0.5 mm. A diameter of the retaining elements is, favorably, at the most 0.2 mm.

So that a wall of the sealing element can be caused to bulge in a simple manner for the purpose of engagement, it is favorable when the retaining elements have a tip pointing away from the protection element.

In order not to damage the sealing element with the retaining element, it is advantageous when the tip is of a conical or spherical shape or when it has a conical or spherical free end. These configurations make it possible to cause a bulge in the desired manner but prevent the sealing element from piercing through. A height of the retaining elements in relation to the respective protection element is, in particular, at the most 1.5 mm. The height of the retaining elements preferably has a value in the range of approximately 0.3 mm to approximately 1.0 mm.

A retaining element, which has a tip with a radius in a range of approximately 0.1 mm to approximately 0.6 mm, can be brought into engagement with the sealing element in a particularly reliable manner.

The retaining elements preferably have a shape which makes it possible for them to become caught in an elastic sealing element.

So that a relative position between the protection elements and the sealing element remains the same irrespective of an opening position of the sealing element, it is favorable when the retaining elements are produced from a material with a high coefficient of static friction. In particular, it would also be conceivable to provide only one surface area with a correspondingly high coefficient of static friction on the protection element so that the sealing element remains adhered to the protection element even in the case of forces acting essentially parallel to its surface and so no relative movement is possible between the protection element and the sealing element.

It is advantageous when the retaining elements are designed in the form of an anti-slide coating or are provided with an anti-slide coating. The anti-slide coating prevents any relative moment of the retaining elements and the protection element, respectively, relative to the sealing element since it prevents any sliding relative to the sealing element.

In accordance with one preferred embodiment of the invention, a connecting device arranged on the base member can be provided for connecting the protection device to the surgical sealing element or the surgical sealing system. The connecting device can, in particular, also undertake the function of securing against rotation in order to prevent any rotation of the protection device about its longitudinal axis, in particular, when it can be brought into engagement with the surgical sealing element or the surgical sealing system in a form-locking manner. Furthermore, such a configuration allows a defined positioning of the protection device relative to the sealing element.

The connecting device may be designed in a particularly simple manner when it comprises at least one connecting element projecting from the base member in a radial direction. For example, the connecting element may be an annular flange which projects from the base member at least partially in a radial direction and extends all the way around or an annular groove which extends all the way around.

Preferably, several connecting elements which are spaced from one another in circumferential direction are provided. The arrangement of connecting elements of this type on the base member makes a defined positioning of the protection device on the sealing element or on another part of the sealing system possible. The connecting elements may be designed in the form of projections protruding at least partially in a radial direction and/or recesses on the base member. For a simple connection of the connecting elements to the sealing element or another part of the sealing system, corresponding elements can be formed on them. Two or more connecting elements may also, of course, be arranged on the base member in circumferential direction so as to be parallel to one another and offset in an axial direction. One of the connecting elements may, for example, secure positioning in an axial direction in the form of an annular flange which extends all the way around, two or more connecting elements, which are offset hereto in an axial direction and spaced from one another in circumferential direction, predetermine an orientation about a longitudinal axis of the protection device and, therefore, also define a device for securing against rotation.

The surgical protection device will be particularly easy to produce when the connecting elements are arranged so as to be distributed uniformly over the circumference of the base member. In addition, assembly will also be particularly easy since the protection device can be arranged and positioned only in defined positions, according to the number of connecting elements provided, relative to the sealing element or to the sealing system.

In order to bring about as uniform a deformation of the protection elements as possible as a result of the insertion of an instrument, it is favorable when the protection elements have a constant thickness along their extension.

The free ends of the protection elements are preferably arranged close to the longitudinal axis in a basic position of the protection device. As a result, it can be ensured that during the insertion of instruments with very small shaft diameters the instruments, first of all, already touch inner surfaces of the protection elements in any case in order to then move the protection elements in a radial direction outwards, whereby the retaining elements can be brought into engagement with the sealing element. The arrangement of the free ends of the protection elements close to the longitudinal axis may be brought about, in particular, in that the protection elements are curved inwardly away from the base member.

In order to ensure that the retaining elements can come into contact with the sealing element immediately after an instrument has been inserted, it is favorable when the free ends of the protection elements are curved somewhat in the direction away from the longitudinal axis. In the basic position, the free ends preferably point away somewhat from the longitudinal axis so that a free end of the retaining elements can, in particular, be at a greater distance from the longitudinal axis than an inner wall section of the respective protection elements from the longitudinal axis. As a result, the free ends can be pushed outwards in a radial direction, for example, as a result of an instrument coming into contact with the protection elements during the insertion of the instrument and so the retaining elements can engage reliably with the sealing element in a simple manner.

It is advantageous when adjacent protection elements partially cover one another in a basic position of the protection device. They can, in particular, cover one another or overlap increasingly in a direction towards their free ends. This ensures that the sealing element can always be covered sufficiently by the protection elements when the sealing element is folded out in conjunction with a widening of the protection device, i.e., in particular, movement of the free ends of the protection elements away from the longitudinal axis in order to prevent any damage to the sealing element by instruments inserted into the sealing system.

In accordance with one preferred embodiment of the invention, it may be provided for the protection elements bearing retaining elements to cover the protection elements without retaining elements at least partially on the outside in a basic position of the protection device. In this way, it can be ensured that the protection elements with their retaining elements can come into contact, first of all, with the sealing element.

In order to facilitate as compact a construction of the protection device as possible, in particular, in a basic position, in which an insertion opening delimited by the protection elements is as small as possible, it is advantageous when protection elements with and without retaining elements are arranged alternatingly on the base member. This simplifies the production and makes only a minimum number of retaining elements necessary in order to achieve the desired effect of the protection device.

A width of the protection elements bearing retaining elements advantageously decreases in the area of the free ends. This makes it possible, in particular, to fit the free ends of the protection elements into corresponding contours of the sealing element, for example, into corresponding wave peaks or wave troughs of a sealing line or sealing lip of the sealing element which surrounds the longitudinal axis in a wave-like manner. It is thus ensured that the free ends of the protection elements reach as far as the sealing line or sealing lip of the sealing element and this positioning can also be brought about by the engagement of the retaining elements irrespective of any widening of the sealing element.

In order to make widening of an insertion opening defined by the protection elements of the protection device possible in a simple manner, it is favorable when the protection elements are pivotally arranged on the base member. This may be brought about, for example, by means of a pivot mounting or also by a film or hinge joint, via which the protection elements are connected to the base member. Alternatively, pivotability could, however, also be achieved by means of a flexible or partially elastic configuration of the protection elements.

It is particularly advantageous when the protection elements are flexible in themselves. This also makes movement of the protection elements possible outwards away from a longitudinal axis of the protection device or also back again towards it. Flexibility of the protection elements is preferably provided in such a manner that the protection elements cannot kink as a result of instruments inserted.

In principle, it would be conceivable to design the protection device in two or more parts. It is, however, preferably designed in one piece. This makes it possible to produce the protection device in a single production step, whereby this will be simple and inexpensive.

The protection device is favorably produced from a sterilizable material. The material can preferably be steam and/or gamma sterilized.

The protection device may be produced particularly inexpensively when it is produced from a plastic material. It can then be produced, in particular, from one part by way of injection molding.

The surgical sealing system preferably comprises one of the protection devices described above. With such a protection device, the handling and operation of the sealing system is also improved in the manner respectively described.

In accordance with one preferred embodiment of the invention, it may be provided for the sealing element to be designed for the purpose of sealing shafts of elongated surgical instruments during their insertion into a human or animal body, to define a longitudinal axis and to have an opening which is variable in diameter and oriented transversely or essentially transversely to the longitudinal axis and through which a shaft can be inserted. In a basic position, the sealing element is preferably designed such that it defines a minimum diameter of the opening. During the insertion of an instrument, the sealing element can preferably be widened such that its opening is adapted to a diameter of the shaft and completely seals it so that no fluid, either gases or liquids, can pass between the shaft and the sealing element.

It is favorable when the sealing element comprises a flexible wall which is closed in a ring shape, when the wall has a first and a second edge each closed upon itself and when the first edge delimits the opening. The first edge can define, form or bear, in particular, a sealing line or a sealing lip so that an optimum sealing of an inserted instrument shaft can be achieved, in particular, in order to avoid any loss of gas when the sealing system is used during a minimally invasive operation of the abdomen.

A particularly good seal can be achieved when the sealing element comprises a flexible wall which is closed in a ring shape, when the wall has a first and a second edge each closed upon itself and when the first edge delimits the opening.

The wall can favorably be folded in a wave-like manner and in a sealing position is folded in a wave-like manner without any kinks with fold lines extending in the direction towards the first edge in such a manner that the first edge defines a wave line which is located entirely on a cylindrical surface. The first edge makes it possible, in particular, to seal instruments which are circular in cross section perfectly. The first edge defining a wave line surrounds an instrument shaft, wherein, in contrast to conventional sealing elements, it does not define a circular abutment on the instrument shaft but rather a sealing line which is in a ring shape closed upon itself and wave-like in a side view. The first edge can, in particular, also bear a sealing lip and be otherwise designed in the form of a bead in order to achieve a particularly good and defined seal relative to an inserted instrument shaft.

In order to improve the sealing properties further, it is advantageous when the cylindrical surface is oriented concentrically to the longitudinal axis.

So that an optimum sealing of shafts with minimum diameters can already be ensured, it is favorable when the sealing element, in a basic position, takes up a sealing position, in which the opening has a minimum diameter.

It is advantageous when the sealing element has, in the basic position, a wall which is folded in the direction towards the first edge in a wave-like manner without any kinks and when the first edge defines a wave line which is located entirely on a cylindrical surface. In this way, an instrument shaft can be sealed perfectly by the sealing element after its insertion.

In accordance with one preferred embodiment of the invention, it may be provided for the wave line to have wave peaks above a plane of the opening which extends at right angles to the longitudinal axis and wave troughs below the plane of opening. The height of the wave peaks and wave troughs, respectively, in relation to the plane of opening may vary optionally as a function of a diameter of the opening, depending on the shaft inserted. In the optimum case, the original wave line transfers into a circular line when the opening is widened to its maximum width.

In order to achieve an optimum protection of the sealing element, it is advantageous when the free ends of the protection elements bearing retaining elements engage between the wave peaks and wave troughs. The protection elements thus protect the sealing element against damage up to the wave line.

The production of the sealing system will be particularly simple when the protection device can be connected detachably to the sealing element. In this way, it may be ensured, in addition, that the protection device can be positioned on the sealing element in an optimum way in order to protect it in an optimum manner from instruments inserted. In addition, the sealing element can be replaced in a simple manner.

A simple connection of the protection device to the sealing element can be achieved, in particular, in that the sealing element has connecting members corresponding to the connecting elements of the connecting device. The connecting members may be designed in the form of projections and/or recesses, in which the connecting elements preferably engage in a form-locking manner.

In order to bring about an optimum sealing of instrument shafts, also when they are inserted at an angle in relation to a longitudinal axis of the sealing system, it is advantageous when the connecting members are arranged on the sealing element so that they can tilt, pivot or be inclined in relation to a plane extending transversely to the longitudinal axis thereof. This configuration has the advantage that a protection device mounted on the sealing element can also exercise its function in an optimum manner, in particular, during deflection of an instrument. The connecting elements held in the connecting members result in the base member of the protection device also being pivoted, tilted or inclined accordingly when the sealing element is tilted. Vice versa, the protection device can also incline the sealing element accordingly during any tilting of instruments or support a deflection movement of the entire sealing element. Particularly during any unfolding of a sealing element described above with a wall folded in a wave-like manner, this is advantageous in order not to draw up the sealing element on account of slight radial, circumferential tensions.

The connecting elements and connecting members are advantageously arranged in circumferential direction to correspond to the wave line. In this way, it can be ensured that free ends of the protection elements of the protection device reach only as far as the wave line and do not cover it which would make sealing of an inserted instrument shaft impossible. In addition, it can also be ensured in this way that the protection elements always reach as far as the wave line, for example, by dipping their free ends into wave troughs and can, therefore, protect the sealing elements from damage essentially completely.

The sealing system favorably comprises a sealing element holder for holding the sealing element; this sealing element holder can be connected detachably to the trocar sleeve. It is thus possible, in particular, to hold the sealing element prior to insertion into the trocar sleeve or into a corresponding receptacle of a sealing element holder which improves handling of the sealing system altogether. Furthermore, assembly of the sealing system is also made easier.

The trocar sleeve preferably has a sealing element holder receptacle for the insertion of the sealing element holder. It is thus possible to assemble the parts of the sealing system simply and reliably.

The sealing element holder favorably comprises a holder sealing element for sealing the sealing element holder with respect to an inner wall surface of the trocar sleeve. In this way, fluid losses, in particular, gas losses can be prevented by the sealing system. A fluid channel defined by the trocar sleeve is thus sealed in an optimum manner, on the one hand, by the holder sealing element and, on the other hand, by the sealing element inserted into the sealing element holder. The sealing element holder has, in addition, the advantage that parts of the sealing system subject to wear, for example, the sealing element can be replaced, in particular, in a simple manner.

The sealing element holder can be sealed relative to the trocar sleeve in a simple and reliable manner when the holder sealing element abuts on an annular surface of the trocar sleeve which points in a proximal direction or essentially in a proximal direction.

The construction of the sealing system will be particularly simple when the annular surface is defined by a one-step narrowing of an inner diameter of the trocar sleeve. The narrowing of the diameter can, in particular, be formed in the direction towards a distal end of the trocar sleeve.

The sealing system will be particularly simple to produce when the holder sealing element is designed in one piece with the sealing element holder. The holder sealing element, like the entire sealing element holder, can be produced, in particular, from a plastic material and so the sealing element holder can, for example, be injection molded altogether from a plastic material as one part. This simplifies, in addition, the assembly of the sealing system since no additional component is required and has to be mounted in order to seal the sealing element holder relative to the trocar sleeve. The insertion of the sealing element holder with a sealing element held therein into the trocar sleeve is sufficient for sealing. No additional steps are required for this.

The holder sealing element is preferably designed in the form of a flange projecting in a radial direction from the sealing element holder. A flange of this type can be produced in a simple manner and, in particular, ensure an optimum sealing of the trocar sleeve relative to the sealing element holder by way of corresponding abutment on an annular surface which extends transversely or essentially transversely to the longitudinal axis of the sealing system and is, optionally, also inclined.

In order to be able to compensate, in particular, for manufacturing tolerances during the production of the parts of the sealing system, it is favorable when the flange is inclined somewhat in a distal direction in relation to a plane extending transversely to the longitudinal axis. The holder sealing element can thus be pressed, in particular, in a pretensioned manner against a corresponding (sealing) surface of the trocar sleeve during the insertion of the sealing element holder.

A particularly good sealing of the sealing element holder relative to the trocar sleeve can be achieved, irrespective of any manufacturing tolerances of individual parts of the sealing system, when the holder sealing element can be deformed elastically at least in sections. An edge of the holder sealing element can, in particular, form a sealing lip and abut on any optional inner surface of the trocar sleeve.

The sealing element is favorably produced from a plastic material, preferably from a plastic material which can be sterilized by steam and/or gamma rays. It is advantageous when the plastic material is or contains an elastomer, in particular, silicone or polyisoprene. As a result, the retaining elements of the protection device can be brought into engagement with the sealing element particularly well.

In order to avoid any damage to the sealing element and, nevertheless, allow a deformation of the sealing element, which is required for avoiding any relative movement between the sealing element and the protection device, by the retaining elements, it is advantageous when the sealing element consists of a material with a Shore hardness in a range of approximately 20 A to approximately 60 A.

The wall thickness of the sealing element is preferably in a range of approximately 0.2 mm to approximately 0.8 mm. A sealing element with a wall thickness in the specified range allows it to be deformed or caused to bulge by the retaining elements in the desired manner described above in order to avoid any relative movement between the sealing element and the protection device in the area of the retaining elements.

A trocar system provided altogether with the reference numeral 10 and forming a surgical sealing system is illustrated in FIGS. 1 to 13. It comprises a trocar sleeve 14 which defines a longitudinal axis 12 and has a seal housing 16 and a shaft 18 extending away from it in a distal direction, a seal arrangement 20 arranged in the seal housing 16 as well as an obturator 22 which has a distal end especially formed for severing and expanding body tissue and is pushed into the trocar sleeve 14 prior to the insertion of the trocar sleeve 14 into the body of a patient in order to facilitate the insertion of the trocar sleeve 14 into the body of the patient.

The trocar sleeve 14 is designed to be essentially rotationally symmetric and defines a receptacle 24 for the seal arrangement 20 in the interior of the seal housing 16. A minimum inner diameter of the trocar sleeve 14 is defined by the shaft 18. In a first area of transition 26 from the shaft 18 to the seal housing 16, the inner diameter of the shaft 18 enlarges continuously and remains constant in the area of a first enlargement space 28. The first enlargement space 28 is adjoined by a second area of transition 30, in which the inner diameter of the trocar sleeve 14 again enlarges continuously as far as a distal part 32 of the receptacle 24.

Figure 3:
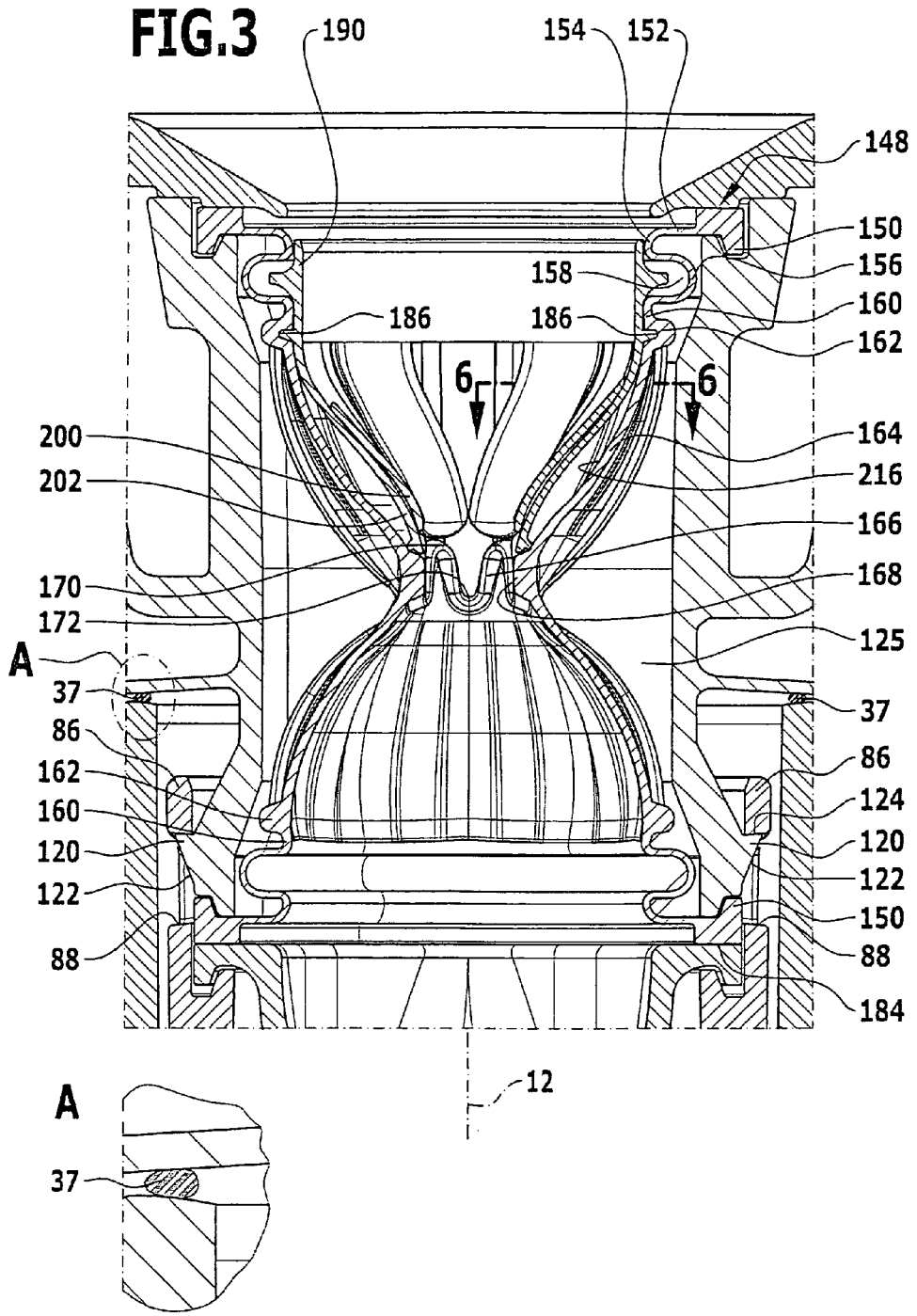
FIG. 3: shows an enlarged partial view of the sectional view in FIG. 2.
Figure 4:
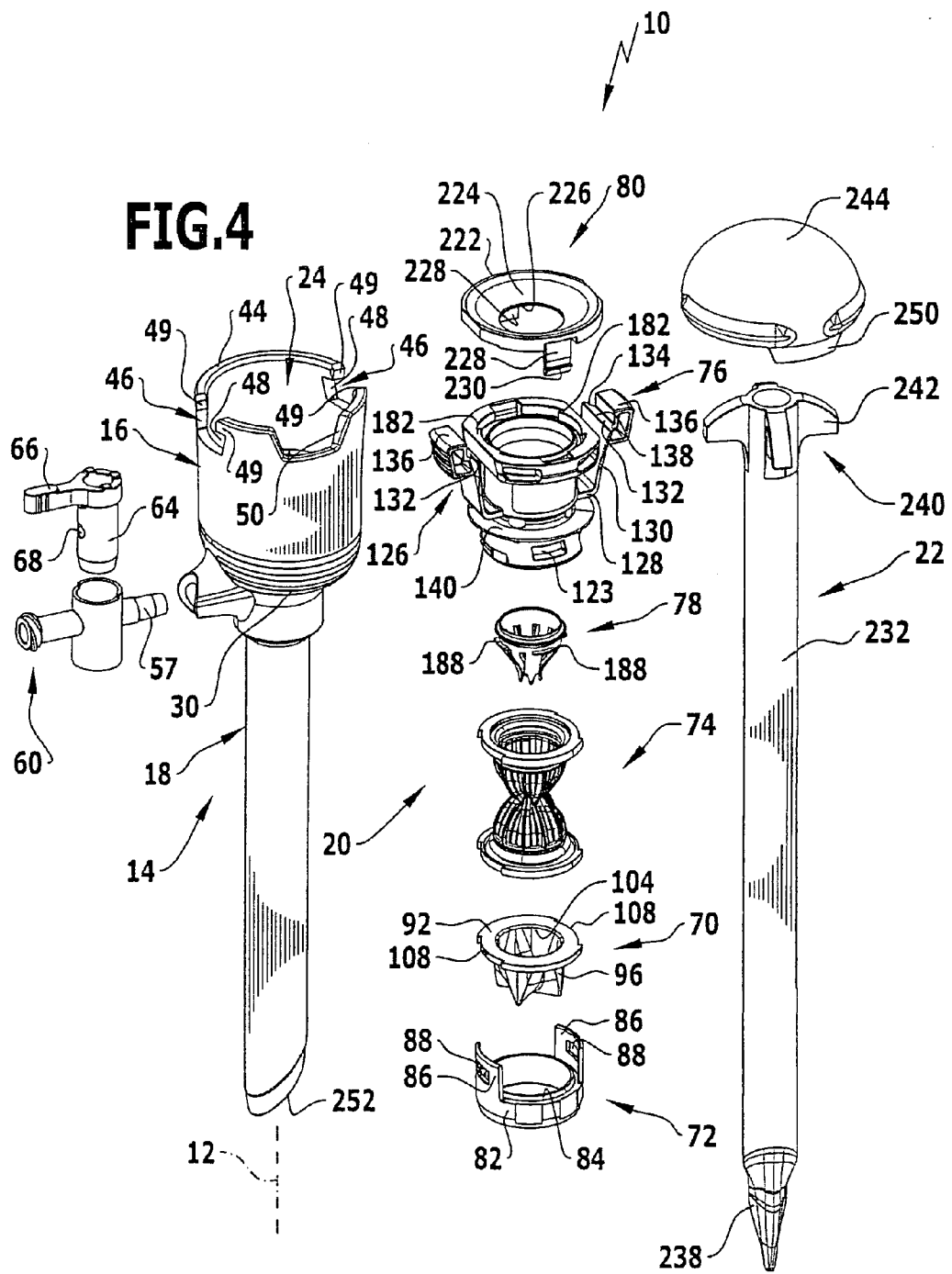
FIG. 4: shows a perspective exploded illustration of the sealing system from FIG. 1.
Figure 5:
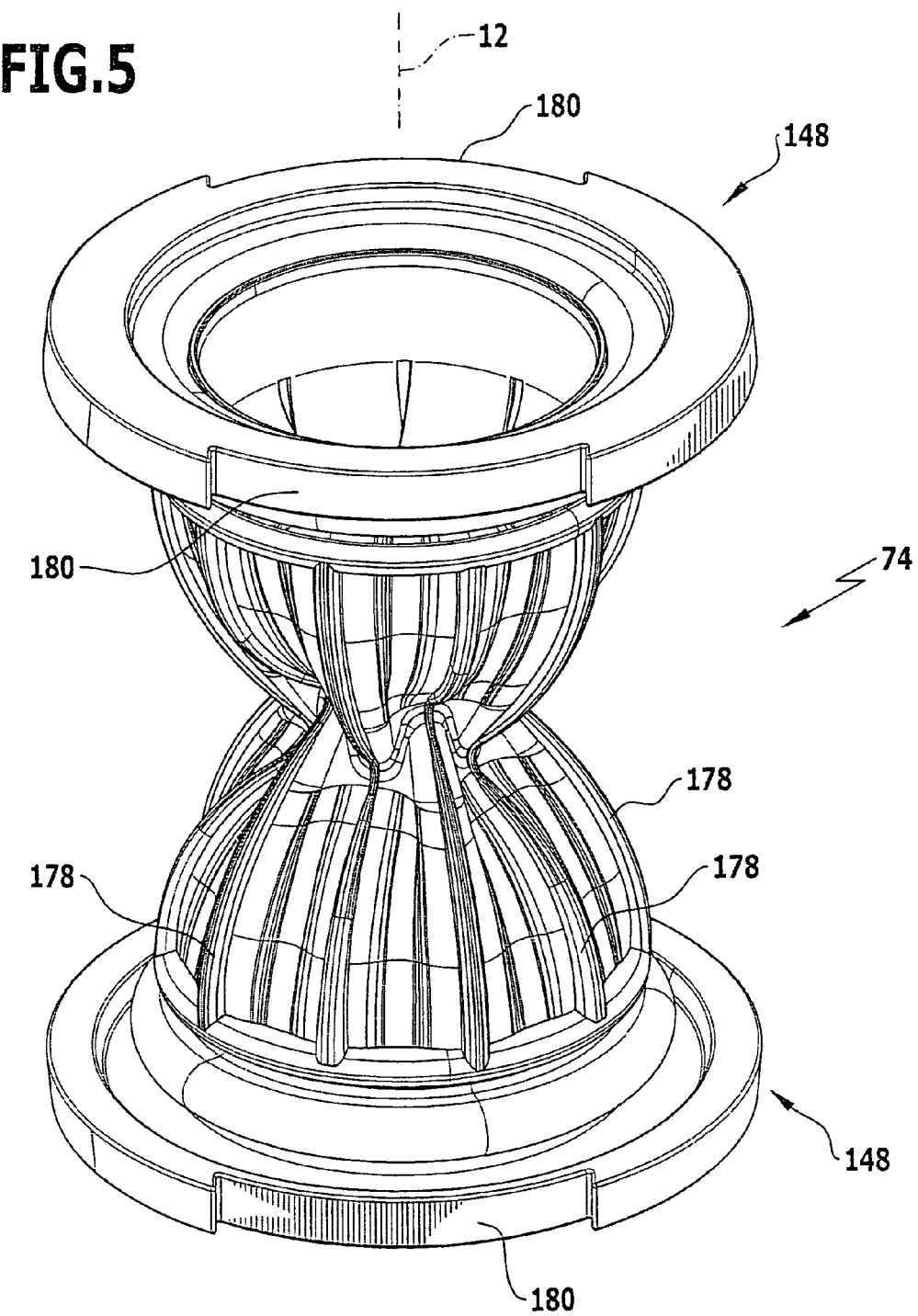
FIG. 5: shows a perspective view of the sealing element from FIG. 4.

An inner diameter of the seal housing 16 enlarges in one step during the transition from the distal part 32 to a proximal part 34 thereof so that an annular surface 36 is defined which points in a proximal direction. The annular surface can optionally bear an additional seal 37 which is produced by injection molding an elastomer and is illustrated in FIG. 3, for example, by dotted lines. A flat recess 38 in the annular surface therefore defines a flat sealing surface 40 which projects somewhat in a proximal direction and is separated from an inner wall 42 of the proximal part 34 by the recess 38.

Proceeding from a proximal end 44 of the seal housing 16, two locking receptacles 46 are formed, which are symmetric to one another, located diametrically opposite one another with respect to the longitudinal axis 12 and each have two lateral undercuts 48 which are open in directions opposite to one another in circumferential direction. The locking receptacles 46 form part of a snap-in connection, with which the seal arrangement 20 can be locked in the seal housing 16, as will be explained in detail in the following.

Figure 12:
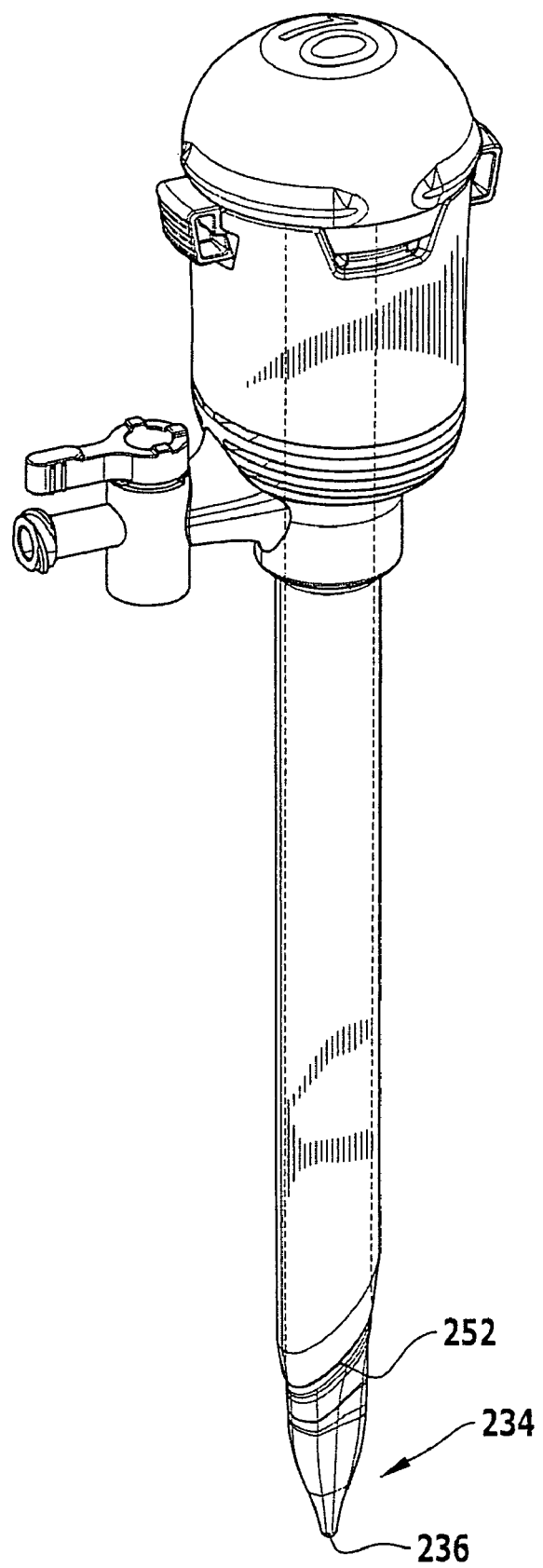
FIG. 12: shows a view analogous to FIG. 1 of the sealing system with obturator inserted.
Figure 13:
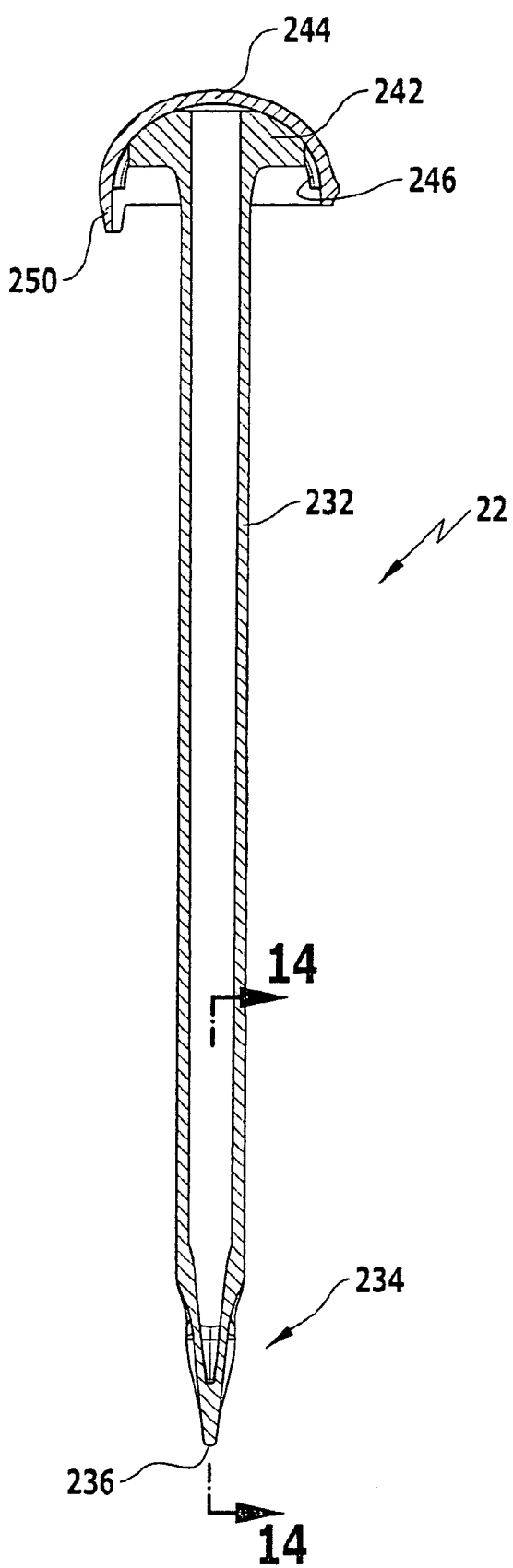
FIG. 13: shows a longitudinal sectional view of the obturator illustrated in FIG. 12.
Figure 14:
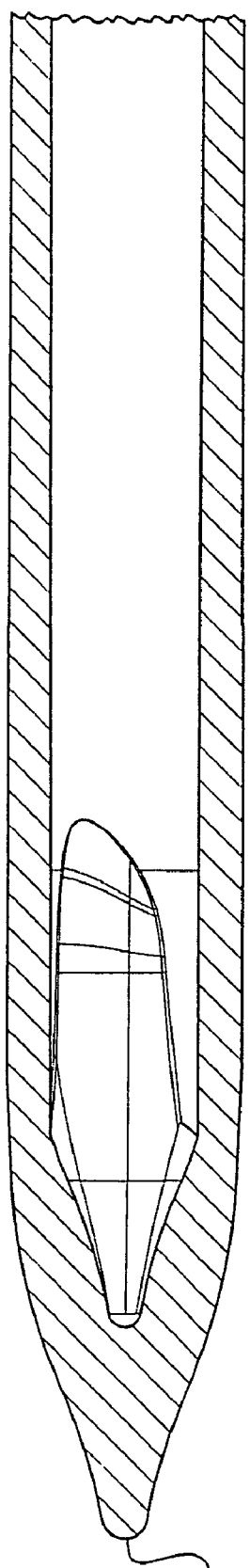
FIG. 14: shows a sectional view along line 14-14 in FIG. 13.

Furthermore, proceeding from the end 44, a recess 50 narrowing somewhat in a distal direction is formed symmetrically between the locking receptacles 46 in a wall 52 of the seal housing 16 and a corresponding projection 250 of the obturator 22 engages in the recess when the obturator 22 is inserted fully into the trocar sleeve 14, as illustrated in FIG. 12.

A short connection piece 54 is integrally formed on the seal housing 16 on one side in the area of the second area of transition 30 and defines a channel 56 which extends at right angles to the longitudinal axis 12. A connection piece 57 of a closure element 58 is pushed into the channel 56 and has a standardized Luer lock connection 60 which projects in an opposite direction. The closure element 58 comprises a cylindrical valve housing 62, into which a cylindrical closing plunger 64 is inserted, which has a corresponding design and an actuating lever 66 integrally formed thereon. The closing plunger 64 is provided with a bore 68 so that the channel 56 for fluids can be opened or closed as a function of a rotary position of the closing plunger 64 relative to the valve housing 62. Instead of the closure element 58 described, other optional types of known closure elements can also be provided, in particular, also special, spring-loaded and, therefore, self-locking Luer lock connections.

The seal arrangement 20 comprises two seals, namely a cross recessed valve 70 which is held on a holder ring 72 as well as a sealing element 74 which is described in detail in its principal construction in German Utility Model 20 2006 005 442. The description in this publication is incorporated herewith in its entirety into the present description.

The sealing element 74 is held in the interior of a sealing element holder 76 which can be connected detachably to the holder ring 72. On the proximal side, a protection device 78 is detachably held on the sealing element 74 so that the sealing element 74 can be removed from the sealing element holder 76 together with the protection device 78 as required. On the proximal side, the sealing element holder 76 can be closed by a cover 80.

The individual parts of the seal arrangement 20 will be described in greater detail in the following.

The holder ring 72 comprises a ring 82 which is circular in cross section and from the edge of which on the proximal side an annular flange 84 is formed which projects in a proximal direction but does not extend over the entire width of a wall of the ring 82 but rather only over about half of it. Furthermore, two connecting wings 86 designed symmetrically to one another project in a proximal direction from the proximal edge of the ring 82, located diametrically opposite one another with respect to the longitudinal axis 12. The connecting wings 86 each have two essentially rectangular openings 88 which are oriented transversely to the longitudinal axis 12. The connecting wings 86 are arranged at a certain distance from the flange 84 so that a groove 90 is formed between the flange 84 and each of the connecting wings 86.

The cross recessed valve 70 comprises, on the proximal side, an annular attachment flange 92 which has an annular projection 94 which points in a distal direction and is designed to correspond to the grooves 90 in its height as well as in its outer dimensions. The cross recessed valve 70 further comprises a valve member 96 which projects in a distal direction on the attachment flange 92 and opens on the distal side into a cross-shaped end surface 98 which is provided with two slits 100 at right angles to one another. The valve member 96 is designed in a basic position, as illustrated, for example, in FIGS. 2 and 4, such that the sectional surfaces 102 of the valve member 96 which are separated by the slits 100 abut directly on one another and thus close an annular opening 104 defined by the attachment flange 92 completely, somewhat on the distal side of the attachment flange 92. The valve member 96 is, on the proximal side, integrally formed directly on an inner edge of the attachment flange 92 so that an annular groove 106, in which the flange 84 can engage essentially in a form-locking manner, is formed between the valve member 96 and the annular projection 94.

The attachment flange 92 is provided, in addition, with two recesses 108, which point in a radial direction and in which the connecting wings 86 engage when the valve member 96 is inserted into the holder ring 72, and projects beyond an edge of the ring 82 on the distal side at least partially with the valve member 96, in particular, with its end surface 98 having the slits 100.

The sealing element holder 76 is of an essentially elongated, sleeve-like design. It comprises a central sleeve member 110 which is formed coaxially to the longitudinal axis 22. An inner surface 112 of the sleeve member 110 is designed to be completely rotationally symmetric. The inner surface 112 defines and delimits a longitudinal channel 114, into which the sealing element 74 is inserted. An inner diameter of the sleeve member 110 widens somewhat towards the respective distal and proximal ends thereof. Annular projections 116 and 118 are formed on the distal side and on the proximal side, respectively, and these point in a proximal and a distal direction, respectively, in order to be brought into engagement with corresponding flanges and grooves, respectively, on the sealing element 74.

Two snap-in noses 120 are formed on an outer side of the sleeve member 110 somewhat on the proximal side of the annular projection 118 on the distal side. These snap-in noses point in opposite directions, are located diametrically opposite one another with respect to the longitudinal axis 12 and define slide-on surfaces 122, which point outwardly and are inclined somewhat in a distal direction, and, therefore, also an annular edge 124 which points in a proximal direction. The snap-in noses 120 are designed to correspond to the openings 88 in the connecting wings 86. The connecting wings 86 can be pushed over the slide-on surfaces 122 from the distal side so that they pivot outwards somewhat in a radial direction away from the longitudinal axis 12. As soon as the snap-in noses 120 can engage fully in the openings 88, the connecting wings 86 spring back again in the direction towards the longitudinal axis 12. The holder ring 72 and the sealing element holder 76 can be interlockingly connected to one another in the manner described.

Two rectangular openings 123 are provided in the sleeve member 110 between the snap-in noses 120, i.e., offset through 90° relative to them in circumferential direction, these openings connecting an interior space 125 of the sleeve member 110 to an outer side thereof. In this way, a balance of pressure between the interior space 125 and the surroundings of the seal element holder 76 can be achieved. The balance of pressure which can be achieved in this way between a gas pressure prevailing in the body of a patient and the interior space 125 or the deaeration/aeration of the interior space 125 thus possible prevents the sealing element 74 from having to widen against a gas volume in the interior space which would become trapped following assembly of the sealing element 74 on the sealing element holder 76.

In order to connect the sealing element holder 76 to the seal housing 16, two coupling members 126 are arranged so as to project from an outer side of the sealing element holder 76 and be located diametrically opposite one another. They each comprise a transverse web 128, which projects directly from the sleeve member 110 in a radial direction and away from which a spring part 130 extends which extends essentially parallel to the sleeve member 110 in a proximal direction. At a proximal end of the spring part 130, protruding snap-in projections 132 are formed on both sides of the spring part 130 pointing essentially in circumferential direction, these projections each defining slide-on surfaces 134 which point away from the longitudinal axis 12. An operating element 136 essentially in the shape of a parallelepiped is arranged on an outer side of the spring parts 130 between the slide-on surfaces 134 and projects somewhat beyond the end of the spring part 130 on the proximal side.

In order to connect the sealing element holder 76 to the seal housing 16, the distal end of the sealing element holder 76 is inserted into the seal housing 16 until the projections 49 which laterally delimit the undercuts 46 come into contact with the slide-on surfaces 134 and pivot the spring parts 130 somewhat in the direction towards the longitudinal axis 12 as a result of the sliding contact. As soon as a proximal end surface 138 of the spring parts 130 can engage in the undercut 48, the spring parts 130 spring outwards somewhat in a radial direction and the end surface 130 abuts on an edge of the projection 49 pointing in a distal direction. In order to release the sealing element holder 76 from the trocar sleeve 14, the operating elements 136 can be acted upon with a force acting in the direction towards the longitudinal axis 12 so that the spring parts 130 are pivoted in the direction towards the longitudinal axis 12 and the snap-in projections 132 again release the undercut 48. The sealing element holder 76 can then be withdrawn from the seal housing 16 in a proximal direction.

A holder sealing element 140 is formed somewhat to the distal side of the transverse webs 128, namely in the form of an annular flange which projects essentially in a radial direction and is inclined somewhat in a distal direction, namely through about 2° with respect to a transverse plane extending at right angles to the longitudinal axis 12. The holder sealing element 140 has a thickness which predetermines a certain elasticity or flexibility of the holder sealing element 140. It can, therefore, be somewhat elastic in an axial direction and compensate for manufacturing tolerances at the trocar sleeve 14 and the sealing element holder 76. The holder sealing element 140 is arranged on the sealing element holder 76 in such a manner that when the sealing element holder 76 is connected in a snap-in manner to the seal housing 16 in the manner described, a sealing surface 142 of the sealing element holder 76 which points in a distal direction abuts on the annular surface 36, optionally somewhat pretensioned, and thus a perfect sealing of the sealing element holder 76 is achieved with respect to an inner wall 144 of the seal housing 16 of the trocar sleeve. The holder sealing element 140 can optionally bear a further seal 141, which is produced by injection molding an elastomer and drawn in, by way of example, in FIG. 11 as dotted lines, for the purpose of improving the sealing effect.

The sealing element 74 is designed to be essentially rotationally symmetric with respect to the longitudinal axis 12. Furthermore, it is designed to be essentially mirror symmetric with respect to a plane of opening 146 which extends transversely to the longitudinal axis. The plane of opening 146 extends parallel to two flange rings 148 on both sides, which limit the sealing element 74 on the distal side and the proximal side and define a maximum outer diameter of the sealing element 74. Annular projections 150, which can engage around the annular projections 116 and 118 on the outside, project from the flange rings 148 as far to the outside on them as possible and each points in the direction of the other flange ring 148. The sealing element 74 can thus be suspended or tensioned in a simple manner via the annular projections 116 and 118 and held in the interior of the sealing element holder 76.

A first transverse section 152 extends from the flange rings 148 in a radial direction towards the longitudinal axis 12 and merges into a first bead section 154 which is bent back towards the outside and merges, on the other hand, directly into a second bead section 156 which has, on the other hand, an end directed towards the longitudinal axis 12. The second bead section 156 thus defines an annular groove 158 which is open in the direction towards the longitudinal axis.

Figure 6:
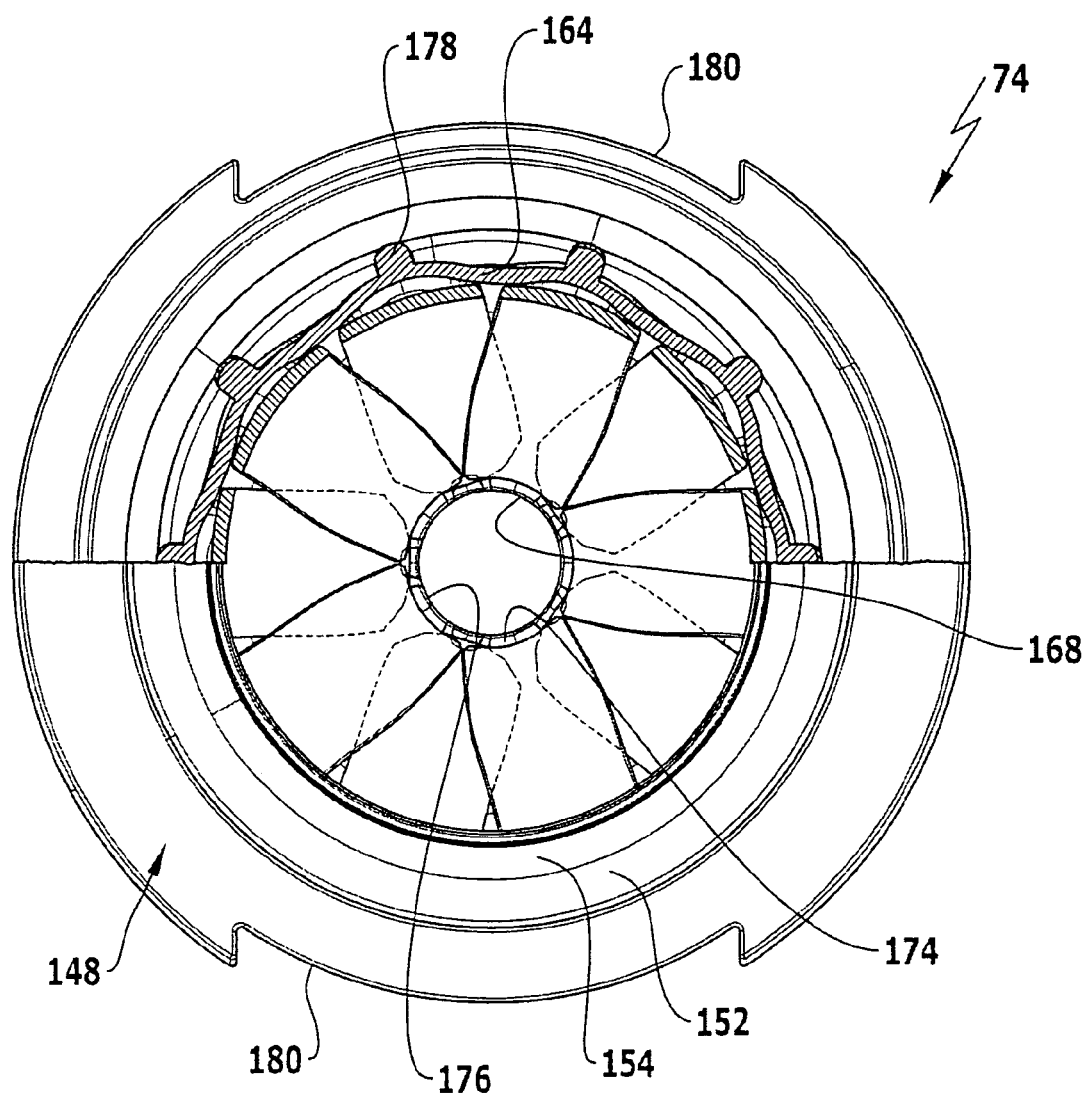
FIG. 6: shows a sectional view along line 6-6 in FIG. 3.

On the distal side, a short cylindrical section 160 adjoins the second bead section 156 and merges into a thickened bead 162 protruding outwards on the sealing element 74. Proceeding from the beads 162, at which a wall 164 of the sealing element 74 projects essentially without folds, the wall 164 is folded like curtains as far as the plane of opening 146. The folding results in a sealing line 166 which, in the form of a wave line, defines wave peaks 170 on the proximal side of the plane of opening 146 and wave troughs 172 on the distal side of the plane of opening 146. The wave line 168 is reinforced somewhat and designed in the form of a sealing lip 174 which is, therefore, located partially on the proximal side and partially on the distal side of the plane of opening 146. It is, however, apparent in a plan view, as illustrated in FIG. 6, that the sealing line 166 and, therefore, also the sealing lip 174 delimit a circular opening 176 of the sealing element 74. The opening 176 has a minimum inner diameter in a basic position, as illustrated, for example, in FIGS. 3 to 6. The opening 176 can, as illustrated, for example, in FIG. 11, be widened to such an extent that an inner diameter thereof corresponds to an inner diameter of the sealing element 74 in the area of the beads 162. The folded wall 164 unfolds at the same time, is practically completely unfolded over the entire length between the beads 162 and thus defines an essentially cylindrical wall surface.

In order to stabilize the sealing element 74, reinforcing ribs 178 are formed on an outer side of the wall 164 proceeding from the beads 164 and reach as far as the sealing lip 166. The sealing element 74 is, altogether, injection molded in one piece from a plastic material which preferably has elastomeric properties. Furthermore, two recesses 180 located diametrically opposite one another are provided on each of the flange rings 148 and are designed to correspond to two projections 182 which project in a radial direction from the sealing element holder 76 in the direction towards the longitudinal axis 12. The recesses 180 in conjunction with the projections 182 form a device for securing against rotation and so the sealing element 74 and the sealing element holder 76 cannot be rotated relative to one another about the longitudinal axis 12 in an assembly position illustrated, for example, in FIGS. 2 and 3.

After the holder ring 72 has been equipped with the cross recessed valve 70, the sealing element holder 76, into which the sealing element 74 is inserted in the manner described above, can be connected to the holder ring 72. On the distal side, an annular end face 184 of the sealing element 74, which points in a distal direction, forms a contact surface for the attachment flange 92. As a result of interlocking connection of the holder ring 72 with the sealing element holder 76 in the manner described above, the attachment flange 92 and the flange ring 148 are pressed against one another and form a perfect seal.

Four recesses 186, which are distributed uniformly over the circumference, are open in a radial direction towards the longitudinal axis 12, form connecting members and serve to accommodate corresponding connecting elements 188 of the protection device 78, are provided at least in the bead 162 on the proximal side. The protection device 78 comprises an annular base member 190 which is closed upon itself and defines a circular opening 192. An annular projection 196 protrudes from the base member 190 in a radial direction outwards, adjacent to a proximal end 194. The connecting elements 188 are arranged somewhat further to the distal side in the form of short, web-like projections. They extend over approximately ⅛ of the overall circumference of the base member 190 and are designed to correspond to the recesses 186. The base member 190 can, therefore, be mounted directly on the sealing element 74, wherein the connecting elements 188 engage in the recesses 168 in a form locking manner for this purpose. They therefore form, at the same time, a device for preventing rotation of the protection device 78 relative to the sealing element 74. Furthermore, they also form a positioning aid for the protection device 78 relative to the sealing element 74.

Figure 8:
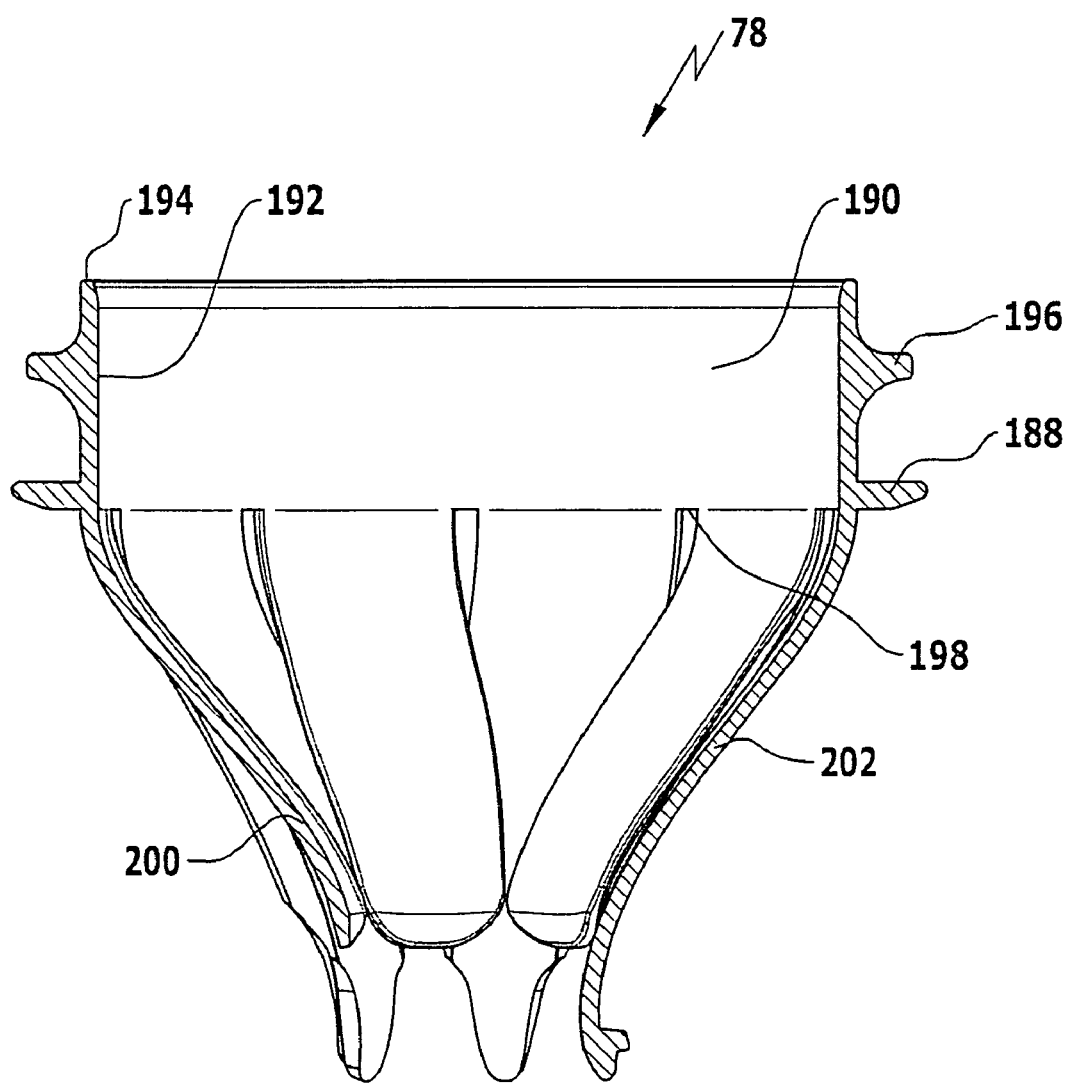
FIG. 8: shows a sectional view along line 8-8 in FIG. 7.
Figure 9:
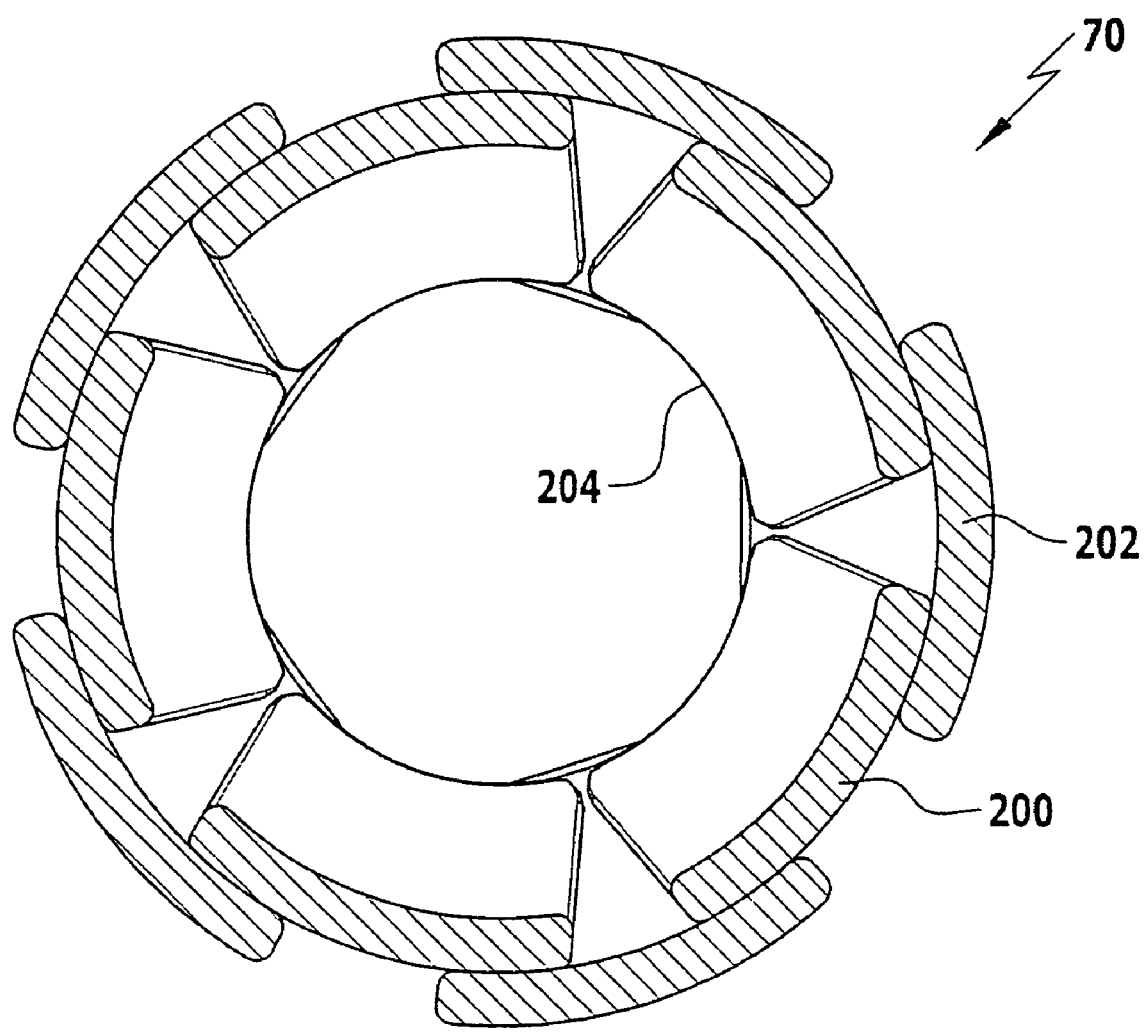
FIG. 9: shows a sectional view along line 9-9 in FIG. 7.
Figure 10:
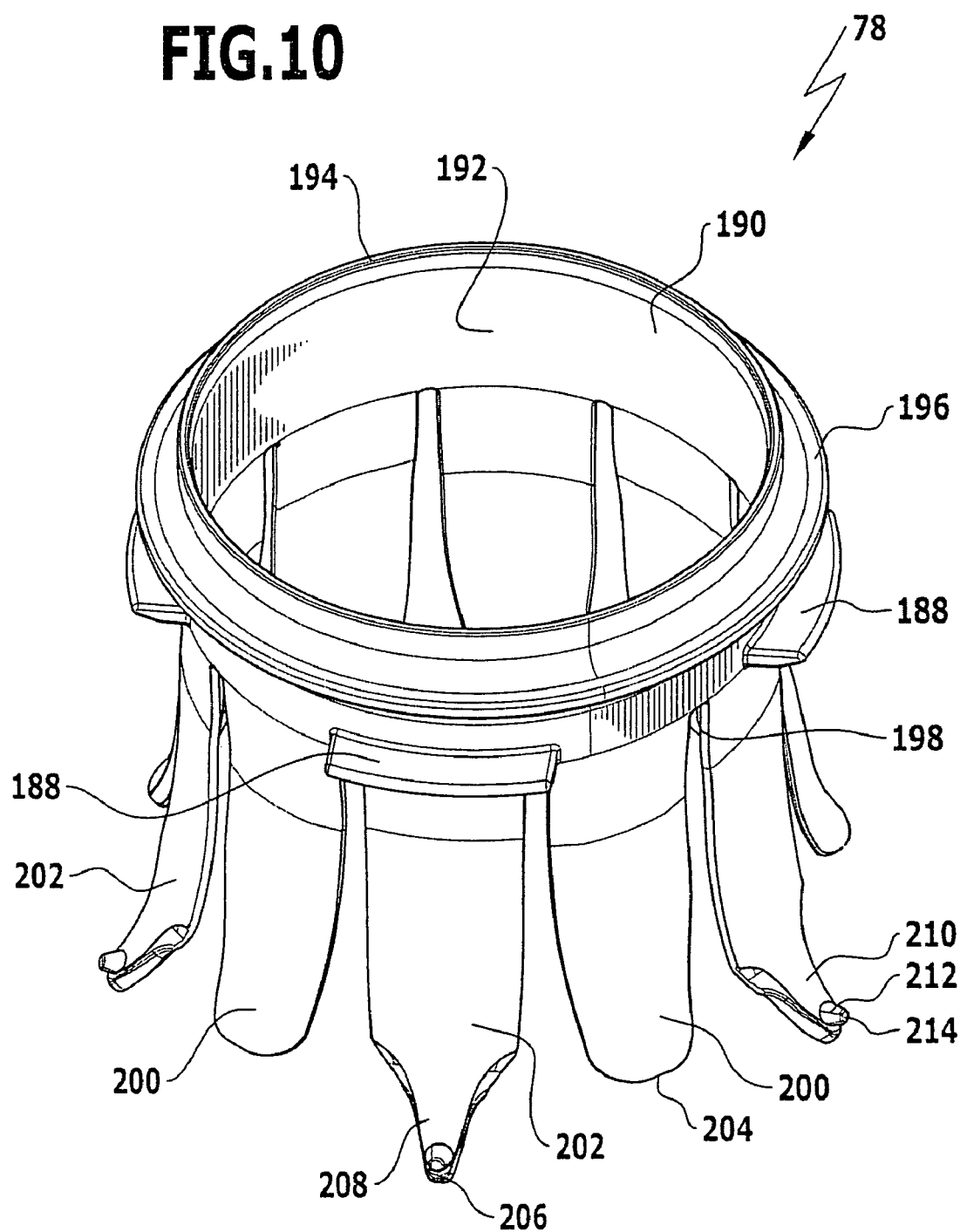
FIG. 10: shows a perspective view of the protection device in a position widened to a maximum.

A total of 10 protection elements, five tongue-like short protection elements 200 and five long protection elements 202, respectively, extend in a distal direction from an edge 198 of the base member 190 on the distal side. They have in a longitudinal section, as illustrated in FIG. 8, a thickness which is constant over their entire length. The short protection elements 200 essentially have more or less the same width up to their free ends 204, the long protection elements 202 approximately to the same length as the short protection elements 200 but then the width of the long protection elements 202 decreases considerably towards their distal end 206 and so a narrow protection element section 208 is formed which is designed, in its outer contour, to correspond essentially to a wave trough 172.

The long protection elements 202 each have a retaining element 212 which projects from an outer side 210 at an angle somewhat in a distal direction and has a length of less than 1 mm. The retaining element is essentially designed in the shape of a truncated cone and has a rounded tip 214.

Figure 7:
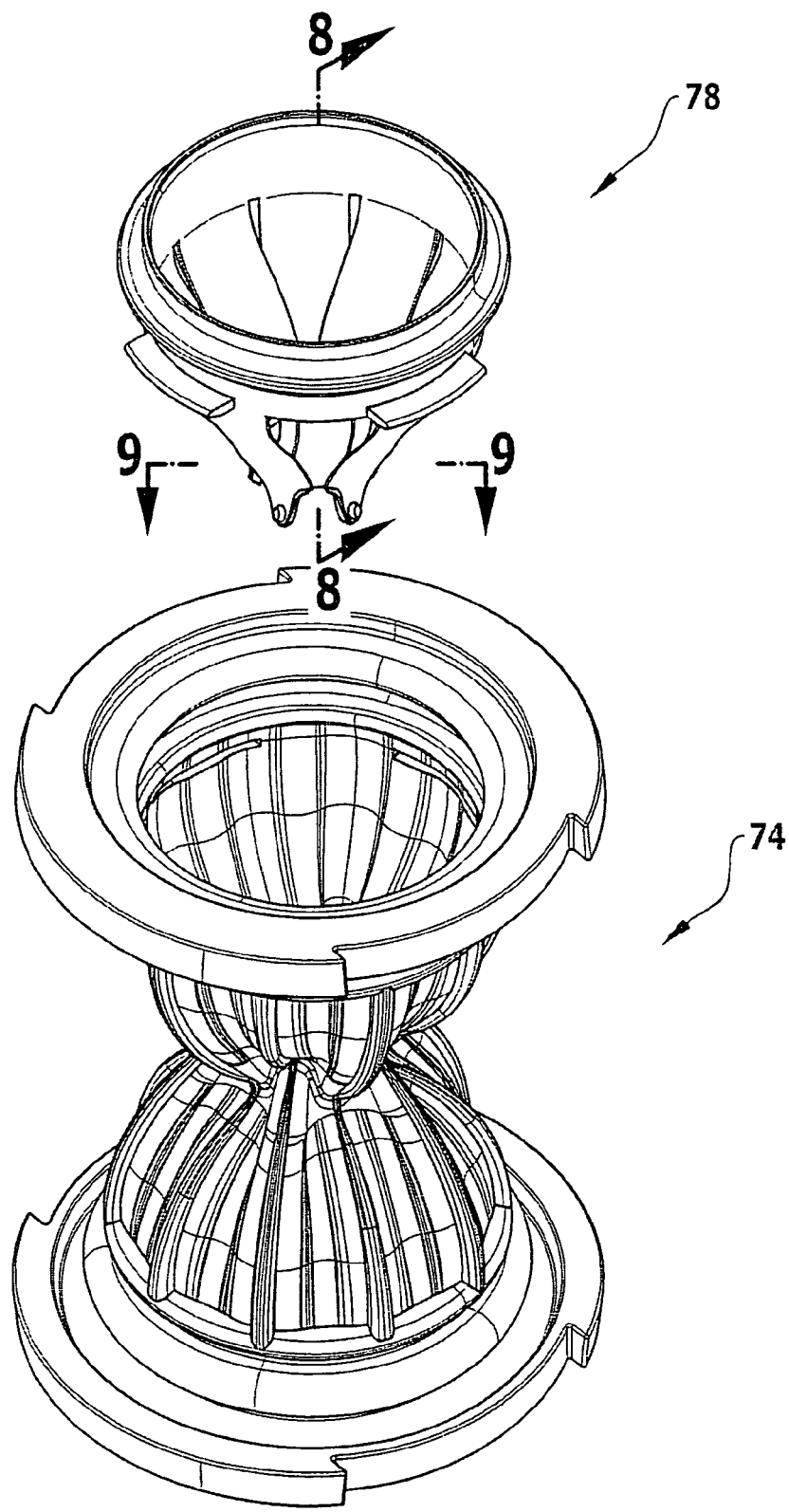
FIG. 7: shows a perspective exploded illustration of a sealing element with protection device.

When the base member 190 is connected to the sealing element 174 in the manner described above, the protection elements 200 and 202, which are flexible on account of their slight thickness, will be folded in the direction towards the longitudinal axis 12 and take up the position illustrated in FIGS. 6 to 8. It should be noted that the long protection elements 202 extend away from the edge 198 on the distal side of the connecting elements 188, the short protection elements 200 in the areas of the edge 198, to which no connecting element 188 corresponds. As a result of the recesses 186 provided accordingly, the protection device 78 can be connected to the sealing element 74 in the correct position; this means that in a basic position all five protection element sections 208 engage in corresponding wave troughs 172. As a result, it is ensured that the distal ends 204 and 206 of the protection device 78 reach, in practice, as far as the sealing line 166 and essentially cover an inner wall surface 216 of the sealing element 74 completely.

In the assembled basic position, the protection elements 200 and 202 already project little from the wall surface 216 on the distal side of the bead 162 and touch it, at the most, close to their ends 204 and 206. In the basic position, the protection elements 200 and 202 are arranged to overlap one another, wherein the short protection elements 200 are located closer to the longitudinal axis 12 than the long protection elements 202. As a result, only the retaining elements 212 touch the wall 164 of the sealing element 74 adjacent to the sealing line 166.

Figure 11:
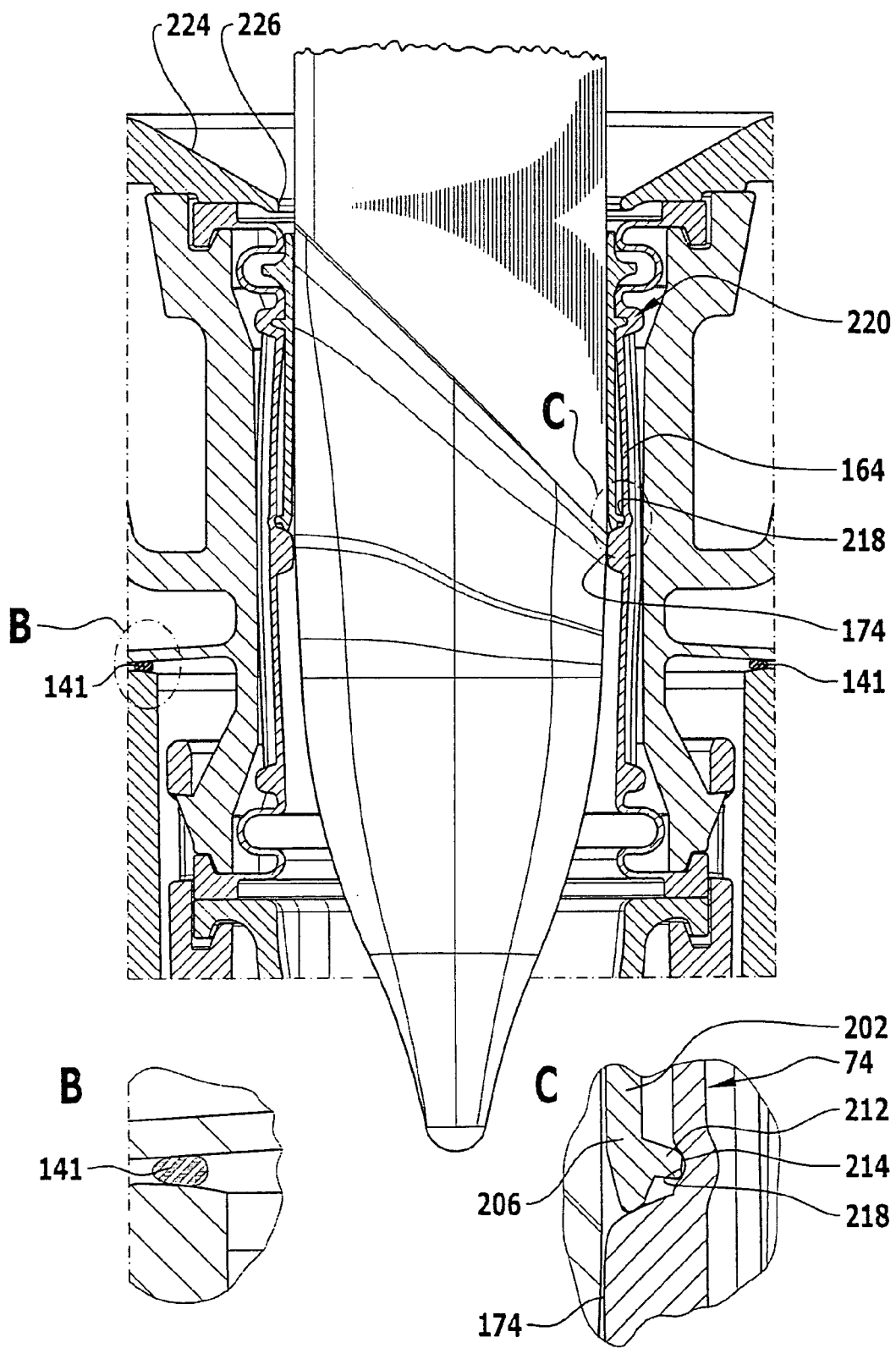
FIG. 11: shows a sectional view analogous to FIG. 3 during the insertion of an obturator of the sealing system.

If an instrument or, as illustrated, for example, in FIG. 11, the obturator 22 is inserted into the sealing element 74 from the proximal side, it comes into contact, first of all, with inner surfaces of the short protection elements 200. If an outer diameter of an instrument, as is the case for the obturator 22, is greater than the opening 176, the short protection elements 200 will be pressed against the long protection elements 202 and pivoted outwards. In this respect, the retaining elements 212 will also be pressed into the wall 164 of the sealing element 74 with their tips 214. This leads to a bulge 218 in the wall 164 due to the retaining elements 212 and so they become caught in the wall 164; it can also be said that the retaining elements 212 and the sealing element 74 are in engagement with one another. As a result of the retaining elements 212 becoming caught in the wall 164, a relative movement of the distal ends 206 of the long protection elements 202 relative to the sealing element 74 is, in practice, prevented. Irrespective of any widening or unfolding of the wall 164 as a function of a diameter of the instrument inserted, the distal ends 206 of the long protection elements 202 always reach as far as the sealing line 166 and protect the sealing element 74 from any possible damage, as described at the outset, as a result of the wall 164 coming into contact with sharp edges of the instruments inserted.

Even when a longitudinal axis of the instrument inserted is tilted somewhat relative to the longitudinal axis 12, the catching effect of the retaining elements 212 remains. As a result of a connecting device 220 formed by the recesses 186 and the connecting elements 188, any tilting of the instrument shaft, which abuts, first of all, on the protection device, will be transferred directly to the sealing element 74, namely in the area of the bead 162 and so the sealing element 74 will be tilted analogously to any tilting of the protection device 78. The special arrangement of the protection device 78 on the sealing element 74 therefore also forms, as it were, an inclination adjustment during the insertion of instruments. The first bead section 154 is suitable, in addition and in particular, for this purpose and this section allows not only a tilting movement but also a transversal movement, at least to the extent that the first bead section 154 is spaced from an inner wall of the sealing element holder 76.

As a result of the curvature of the protection elements 200 and 202 slightly convexly away from the wall 164, it is ensured that an instrument inserted can, first of all, come into contact with distal end areas of the protection elements 200 and 202 before it can touch the sealing lip 174.

The cover 80 serves to close the seal housing 16. It comprises an annular frame 222, from which a cover surface 224, which narrows conically in diameter, extends in the interior and in a distal direction as far as a cover opening 226 which defines a maximum inner diameter of the seal arrangement 20. Instruments with shaft diameters which are greater than an inner diameter of the cover opening 226 cannot be inserted into the trocar sleeve 14. The cover 80 has, in addition, two tongues 228 which point in a distal direction and are located opposite one another and, at free ends, have snap-in projections 230 which can be brought into engagement with corresponding snap-in edges on the sealing element holder 76, which are not illustrated in the Figures. The cover 80 can then be snapped onto the sealing element holder 76 in a simple manner following assembly of the sealing element holder 76 on the seal housing 16.

In order to be able to insert the trocar sleeve 14 into a human or animal body, the obturator 22 is provided. It comprises a hollow shaft 232 which extends coaxially to the longitudinal axis 12, narrows continuously in its outer diameter in a distal end area 234 and defines a rounded tip 236. The end area 234 is not designed to be circular at any point in its cross section but rather non-symmetric as a result of defined recesses 238 which extend parallel to the longitudinal axis 12. In a proximal end area 240, four holder projections 242 are provided on an outer side of the shaft 232, these projections being arranged so as to be offset respectively through 90° relative to one another and serving to mount and connect a cover 244 having essentially the shape of a semi-sphere. Corresponding projections 246 are formed on the cover 244 on an inner side. Optionally, the cover 244 can also be screwed or adhered to the shaft 232 and its holder projections 242. In addition, the tongue-like projection 250 projects from the cover 244 in a distal direction and is designed to correspond to the recess 50 so that the obturator 22 can be inserted into the trocar sleeve 14 with a defined orientation with respect to the longitudinal axis 12. If the obturator 22 is pushed completely into the trocar sleeve 14, the distal end area 234 projects beyond an end face 252 of the shaft 18 which is inclined through approximately 45° with respect to the longitudinal axis 12, as illustrated in FIG. 12.

In the interior of the seal housing 16, sealing is brought about via the sealing element 74 as well as with respect to an outer area of the sealing element holder 76 and the inner wall 144 of the trocar sleeve 14 by means of the holder sealing element 140. If the obturator 22 is removed from the trocar sleeve 14, the cross recessed valve 70 closes a channel which extends along the trocar sleeve 14 in a fluid-tight manner. On account of the outer surfaces of the valve member 96 pointing away somewhat from the longitudinal axis 12, the sectional surfaces 102 will be pressed against one another, in addition, if an overpressure is present in the interior of the body and, therefore, in the area of the shaft 18, in order to close the slits 100. As a result, in the case of laparoscopic operations, during which an overpressure is generated in the abdominal space of a patient by means of a gas in order to keep the operation site free, this overpressure can be maintained even when instruments or, for example, in an analogous manner the obturator 22 are inserted into the interior of the body by means of the trocar system 10.

It is also to be noted that the cross recessed valve 70 can only be opened by means of a distal end of an instrument or, for example, the tip 236 of the obturator 22 when, during the insertion of an instrument, its shaft, for example, the shaft 232 of the obturator 22 is sealed by means of the sealing lip 144 of the sealing element 74. It is thus ensured that either the cross recessed valve 70 will be closed or sealing be brought about by means of the sealing element 74 relative to the instrument inserted.

The trocar sleeve 14, the holder ring 72, the cross recessed valve 70, the sealing element 74, the protection device 78, the sealing element holder 76 as well as the cover 80 are each designed in one piece and preferably injection molded from a sterilizable plastic material. The obturator 22 is designed in two parts, as described, and can likewise be manufactured from a plastic material by way of injection molding.

A gas or a liquid can be introduced into or also withdrawn from the interior of a patient's body through the shaft 18 via the closure element 58 when the closing plunger 64 is in a corresponding position, even when an instrument, for example, the obturator 22 is inserted into the trocar sleeve 14 and a channel defined by the trocar sleeve 14 is sealed on the proximal side of the short connection piece 54.

Figure 15:
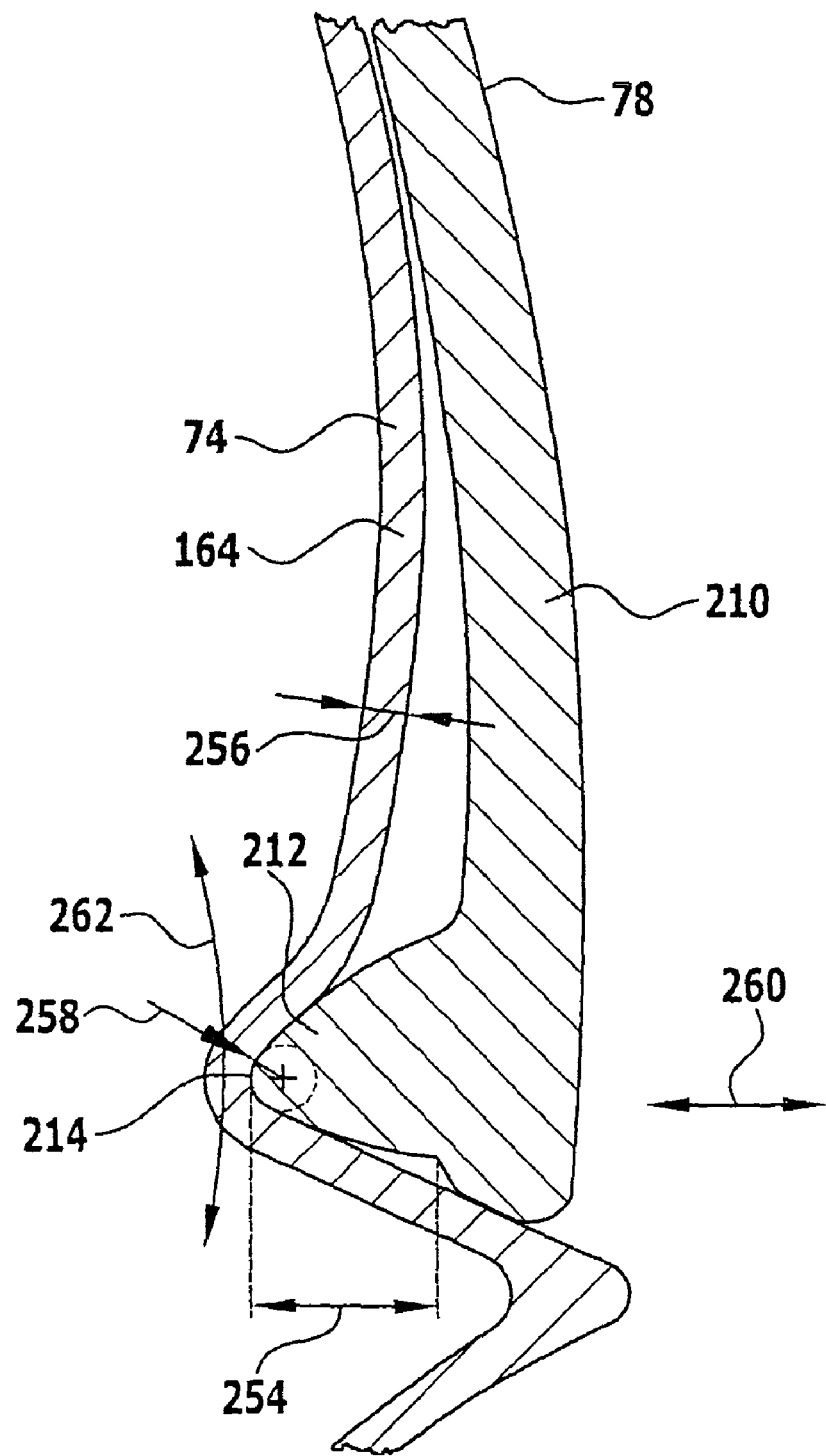
FIG. 15: shows a schematic illustration of the functionality of the protection device and retaining elements thereof in a sectional view similar to Section C in FIG. 6.
Figure 16:
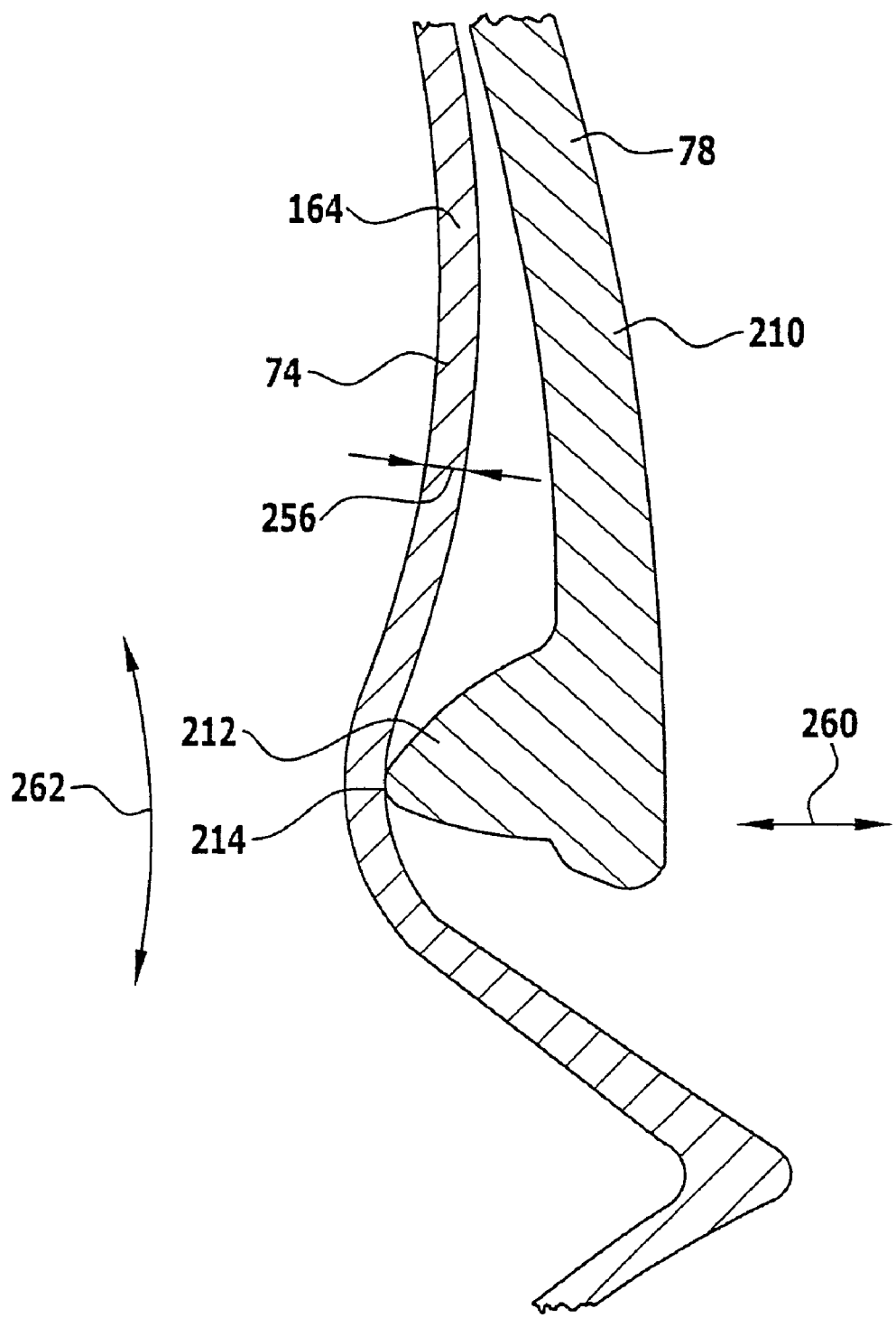
FIG. 16: shows a schematic illustration analogous to FIG. 15 showing a malfunction of the retaining elements of the protection device.

The functionality of the retaining elements 212, in particular, their interaction with the sealing element 74 will be explained in greater detail in conjunction with FIGS. 15 and 16.

If, as already described above, an instrument or the obturator 22, as illustrated, for example, in FIG. 11, is inserted into the sealing element 74 from the proximal side, the retaining elements 212 are also pressed into the wall 164 of the sealing element 74 with their tips 214. For this purpose, it is favorable when a height 254 of the retaining elements in relation to the outer side 210 has a value in the range of approximately 0.3 mm to approximately 1.5 mm and a thickness 256 of the wall 164 has a value in a range of approximately 0.2 mm to approximately 0.8 mm. So that the tip 214 cannot damage the sealing element 74, in particular, not pierce through it, a radius of the preferably semispherical tip 214 of the retaining element 212 is approximately 0.1 mm to approximately 0.6 mm. As illustrated in FIG. 15, the tip 214 is preferably enclosed by the sealing element 74 and is in contact with it areally, whereby as a result of a movement of the protection element 202, in particular, in a direction 260 transverse or essentially transverse to the longitudinal axis 12 a relative movement in a direction 262 at right angles hereto, i.e., parallel or essentially parallel to the longitudinal axis 12 will be avoided. This desired effect will be achieved in a particularly optimum manner when the sealing element is produced from a plastic material, in particular, from an elastomer or contains an elastomer, wherein this can, for example, be silicone or polyisoprene. The desired deformation of the sealing element, i.e., the at least partial surrounding of the retaining element 212 can be improved further when the material, from which the sealing element is produced, has a Shore hardness in a range of approximately 20 A to approximately 60 A.

The bulge 218 in the wall 164 caused by the retaining elements 212 enables the retaining elements 212 to become caught in the wall 164 and so the retaining elements 212 and the sealing element 74 are, as it were, in engagement with one another. A relative movement of the distal ends 206 of the long protection elements 202 relative to the sealing element 74 will, in practice, be prevented by the retaining elements 212 becoming caught in the wall 164.

If the sealing element 74 is, in particular, too thick and not elastic enough or rather too stiff or too hard, the tip 214 cannot cause the desired bulge 218 in the sealing element 74. The at least partial enclosing of the retaining element 212 by the sealing element 74 does not, therefore, take place and so these elements are not in engagement with one another, as illustrated in FIG. 16. As a result, the sealing element 74 and the protection device 78 can be moved relative to one another in the area of the retaining elements 212 which signifies an undesired malfunctioning of the trocar system.

What is claimed is:

1. Surgical protection device for a surgical sealing element of a surgical sealing system comprising a trocar, a surgical sealing element having an insertion opening adapted to be widened, said protection device comprising:
a base member adapted to be arranged on the trocar or on a part of the trocar, the base member being in a ring shape or essentially in a ring shape and defining an opening, and
several protection elements arranged in a circumferential direction on said base member and pointing parallel or towards a longitudinal axis of the protection device,
said protection elements each having a free end pointing essentially in a distal direction,
wherein:
at least some of the protection elements each have a retaining element on an outer side at the free end or in an area of the free end for engagement with an elastic sealing element;
the retaining elements have a shape making it possible for them to become caught in the sealing element;
each of the retaining elements have a tip pointing away from the corresponding protection element; and
the protection elements bearing retaining elements are longer than the protection elements without retaining elements.

2. Surgical protection device as defined in claim 1, wherein the retaining elements each comprise a retaining projection protruding from the protection element.

3. Surgical protection device as defined in claim 2, wherein at least some of the retaining projections protrude from the protection elements at right angles or essentially at right angles.

4. Surgical protection device as defined in claim 2, wherein at least some of the retaining projections protrude away from the protection elements in the area of the free ends at an angle in relation to an extension of the protection elements.

5. Surgical protection device as defined in claim 1, wherein a diameter of the retaining elements is at the most 1 mm.

6. Surgical protection device as defined in claim 1, wherein the tip is of a conical or spherical shape.

7. Surgical protection device as defined in claim 1, wherein the retaining elements are produced from a material with a high coefficient of static friction.

8. Surgical protection device as defined in claim 1, wherein the retaining elements are designed to have an anti-slide coating or are provided with an anti-slide coating.

9. Surgical protection device as defined in claim 1, further comprising a connecting device arranged on the base member for connecting the protection device to the surgical sealing element or the surgical sealing system.

10. Surgical protection device as defined in claim 9, wherein the connecting device comprises at least one connection element projecting from the base member in a radial direction.

11. Surgical protection device as defined in claim 10, wherein several connecting elements spaced from one another in a circumferential direction are provided.

12. Surgical protection device as defined in claim 11, wherein the connecting elements are arranged so as to be distributed uniformly over a circumference of the base member.

13. Surgical protection device as defined in claim 1, wherein each of the protection elements have a constant thickness along an extension of the protection elements.

14. Surgical protection device as defined in claim 1, wherein the free ends of the protection elements are arranged close to the longitudinal axis in a basic position of the protection device.

15. Surgical protection device as defined in claim 1, wherein the free ends of the protection elements are curved somewhat in a direction away from the longitudinal axis.

16. Surgical protection device as defined in claim 1, wherein adjacent protection elements partially cover one another in a basic position of the protection device.

17. Surgical protection device as defined in claim 1, wherein the protection elements bearing retaining elements cover the protection elements without retaining elements at least partially on an outside in a basic position of the protection device.

18. Surgical protection device as defined in claim 1, wherein protection elements with and without retaining elements are arranged alternatingly on the base member.

19. Surgical protection device as defined in claim 1, wherein a width of the protection elements bearing retaining elements decreases in the area of the free ends.

20. Surgical protection device as defined in claim 1, wherein the protection elements are pivotally arranged on the base member.

21. Surgical protection device as defined in claim 1, wherein the protection elements are flexible.

22. Surgical protection device as defined in claim 1, wherein the protection device is designed in one piece.

23. Surgical protection device as defined in claim 1, wherein the protection device is produced from a sterilizable material.

24. Surgical protection device as defined in claim 1, wherein the protection device is produced from a plastic material.

25. Surgical sealing system, comprising:
a trocar with a trocar sleeve,
a surgical sealing element having an insertion opening adapted to be widened and being held on the trocar sleeve for sealing the insertion opening during insertion of a surgical instrument, and
a surgical protection device for the sealing element, said protection device comprising:
a base member adapted to be arranged on the trocar or on the sealing element, the base member being in a ring shape or essentially in a ring shape and defining an opening, and
several protection elements arranged in a circumferential direction on said base member and pointing parallel or towards a longitudinal axis of the protection device,
said protection elements each having a free end pointing essentially in a distal direction,
wherein:
at least some of the protection elements each have a retaining element on an outer side at the free end or in the area of the free end for engagement with the sealing element;
the retaining elements have a shape making it possible for them to become caught in the sealing element;
each of the retaining elements have a tip pointing away from the corresponding protection element; and
the protection elements bearing retaining elements are longer than the protection elements without retaining elements.

26. Surgical sealing system as defined in claim 25, wherein the retaining elements each comprise a retaining projection protruding from the protection element.

27. Surgical sealing system as defined in claim 25, wherein the sealing element is designed for the purpose of sealing shafts of elongated surgical instruments during insertion into a human or animal body, defines a longitudinal axis and has an opening variable in diameter and oriented transversely or essentially transversely to the longitudinal axis, a shaft being insertable through said opening.

28. Surgical sealing system as defined in claim 25, wherein the sealing element comprises a flexible wall closed in a ring shape, wherein the wall has a first and a second edge each closed upon itself and wherein the first edge delimits the opening.

29. Surgical sealing system as defined in claim 28, wherein the wall is adapted to be folded in a wave-like manner and in a sealing position is folded in a wave-like manner without any kinks with fold lines extending in a direction towards the first edge in such a manner that the first edge defines a wave line located entirely on a cylindrical surface.

30. Surgical sealing system as defined in claim 29, wherein the cylindrical surface is oriented concentrically to the longitudinal axis.

31. Surgical sealing system as defined in claim 25, wherein in a basic position the sealing element takes up a sealing position, the opening having a minimum diameter in said sealing position.

32. Surgical sealing system as defined in claim 31, wherein in the basic position the sealing element has a wall folded in the direction towards the first edge in a wave-like manner without any kinks and wherein the first edge defines a wave line located entirely on a cylindrical surface.

33. Surgical sealing system as defined in claim 32, wherein the wave line has wave peaks above an opening plane of the opening extending at right angles to the longitudinal axis and wave troughs below the plane of opening.

34. Surgical sealing system as defined in claim 33, wherein the free ends of the protection elements bearing retaining elements engage between at least one of the wave peaks and wave troughs.

35. Surgical sealing system as defined in claim 25, wherein the protection device is adapted to be connected detachably to the sealing element.

36. Surgical sealing system as defined in claim 25, wherein the sealing element has connecting members corresponding to connecting elements of a connecting device.

37. Surgical sealing system as defined in claim 36, wherein the connecting members are arranged on the sealing element so as to be adapted to tilt, pivot or be inclined in relation to a plane extending transversely to the longitudinal axis.

38. Surgical sealing system as defined in claim 36, wherein the connecting elements and connecting members are arranged in a circumferential direction to correspond to the wave line.

39. Surgical sealing system as defined in claim 25, further comprising a sealing element holder for holding the sealing element, said sealing element holder being adapted to be connected detachably to the trocar sleeve.

40. Surgical sealing system as defined in claim 39, wherein the trocar sleeve has a sealing element holder receptacle for insertion of the sealing element holder.

41. Surgical sealing system as defined in claim 40, wherein the sealing element holder comprises a holder sealing element for sealing the sealing element holder with respect to an inner wall surface of the trocar sleeve.

42. Surgical sealing system as defined in claim 41, wherein the holder sealing element abuts on an annular surface of the trocar sleeve pointing in a proximal direction or essentially in a proximal direction.

43. Surgical sealing system as defined in claim 42, wherein the annular surface is defined by a one-step narrowing of an inner diameter of the trocar sleeve.

44. Surgical sealing system as defined in claim 41, wherein the holder sealing element is designed in one piece with the sealing element holder.

45. Surgical sealing system as defined in claim 41, wherein the holder sealing element is designed as a flange projecting in a radial direction from the sealing element holder.

46. Surgical sealing system as defined in claim 45, wherein the flange is inclined somewhat in a distal direction in relation to a plane extending transversely to the longitudinal axis.

47. Surgical sealing system as defined in claim 41, wherein the holder sealing element is adapted to be deformed elastically at least in sections.

48. Surgical sealing system as defined in claim 25, wherein the sealing element is produced from a plastic material which can be sterilized by at least one of steam and gamma rays.

49. Surgical sealing system as defined in claim 25, wherein the sealing element consists of a material with a Shore hardness in a range of approximately 20 A to approximately 60 A.

50. Surgical sealing system as defined in claim 25, wherein a wall thickness of the sealing element is preferably in a range of approximately 0.2 mm to approximately 0.8 mm.

\* \* \* \* \*